United States Patent
Al-Ali et al.

(10) Patent No.: US 9,965,946 B2
(45) Date of Patent: May 8, 2018

(54) SYSTEMS AND METHODS FOR MONITORING A PATIENT HEALTH NETWORK

(71) Applicant: MASIMO CORPORATION, Irvine, CA (US)

(72) Inventors: Yaser Ammar Al-Ali, San Juan Capistrano, CA (US); Jad Adel Wafeeq, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 0 days. days.

(21) Appl. No.: 14/198,350

(22) Filed: Mar. 5, 2014

(65) Prior Publication Data

US 2014/0266790 A1   Sep. 18, 2014

Related U.S. Application Data

(60) Provisional application No. 61/780,794, filed on Mar. 13, 2013.

(51) Int. Cl.
*G08C 17/02* (2006.01)
*G06F 11/00* (2006.01)
(Continued)

(52) U.S. Cl.
CPC .............. *G08C 17/02* (2013.01); *G06F 11/00* (2013.01); *G06F 11/30* (2013.01); *G06F 19/3412* (2013.01)

(58) Field of Classification Search
CPC ...... G06F 19/3412; G06F 11/30; G06F 11/00; G06F 11/07; G06F 11/22; G06F 11/2247;
(Continued)

(56) References Cited

U.S. PATENT DOCUMENTS

| 5,865,832 A * | 2/1999 | Knopp ............... A61F 9/008 351/209 |
| 2008/0202606 A1 * | 8/2008 | O'Hara ............... F16K 37/0083 137/551 |

(Continued)

FOREIGN PATENT DOCUMENTS

| WO | WO 01/34023 | 5/2001 |
| WO | WO 03/054704 | 7/2003 |

(Continued)

OTHER PUBLICATIONS

International Search Report and Written Opinion for International Application No. PCT/US2014/020795, Notification dated Aug. 21, 2014.

(Continued)

*Primary Examiner* — Brian Wilson
(74) *Attorney, Agent, or Firm* — Knobbe Martens Olson & Bear LLP

(57) ABSTRACT

Systems and methods for monitoring physiological monitoring systems are described herein. A communication interface module can be configured to receive from a physiological monitoring system first data based on a snapshot taken of a status of the physiological monitoring system at a first time. A memory module can be configured to store the first data and a baseline associated with the physiological monitoring system. A processor module can be configured to compare the first data with the baseline and to generate a notification if the first data deviates from the baseline by a predetermined amount. A display module can be configured to display a physical location of a plurality of physiological monitoring systems and display the notification.

20 Claims, 17 Drawing Sheets

(51) Int. Cl.
*G06F 19/00* (2018.01)
*G06F 11/30* (2006.01)

(58) Field of Classification Search
CPC ............ G06F 11/2294; G06F 11/3006; G06F 11/3065; G06F 11/32; G06F 11/34; G06F 11/3409; G06F 11/3442; G06F 11/3466; G06F 19/3418; G06F 3/0482; G06F 19/322; G06F 19/327; G06F 19/3406; G06F 11/3055; G06F 11/3082; G06F 11/327; G06F 11/3447; G08C 17/02
USPC ... 340/870.01, 870.09, 539.1, 539.12, 573.1; 700/28, 32, 108, 109
See application file for complete search history.

(56) References Cited

U.S. PATENT DOCUMENTS

| | | | |
|---|---|---|---|
| 2010/0076453 A1* | 3/2010 | Morris | A61F 9/008 606/130 |
| 2010/0312604 A1* | 12/2010 | Mitchell | G06Q 10/06 705/7.13 |
| 2011/0001605 A1* | 1/2011 | Kiani | G06F 19/327 340/5.6 |
| 2011/0105854 A1 | 5/2011 | Kiani et al. | |
| 2011/0289363 A1* | 11/2011 | Gadher | G06F 11/008 714/47.2 |
| 2014/0135588 A1 | 5/2014 | Al-Ali et al. | |
| 2016/0283665 A1 | 9/2016 | Sampath et al. | |

FOREIGN PATENT DOCUMENTS

| | | | |
|---|---|---|---|
| WO | WO 03/054704 A1 * | 7/2003 | |
| WO | WO 2005/010756 | 2/2005 | |

\* cited by examiner

SYSTEMS AND METHODS FOR MONITORING A PATIENT HEALTH NETWORK

RELATED APPLICATION

This application claims the benefit of priority under 35 U.S.C. § 119(e) of U.S. Provisional Patent Application No. 61/780,794, filed on Mar. 13, 2013, and entitled "SYSTEMS AND METHODS FOR MONITORING A PATIENT HEALTH NETWORK," the disclosure of which is hereby incorporated by reference in its entirety.

BACKGROUND

Field

This disclosure relates to systems, devices, and methods with applications in, for example, hospitals and other patient care facilities. For example, the systems, devices, and methods described herein can be used for monitoring a system that acquires physiological information from patients, analyzes the physiological information, and communicates the physiological information to clinicians and other systems or devices.

Description of the Related Art

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, SpO$_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

The patient monitoring devices may obtain and analyze a large amount of data (e.g., physiological parameters for one or more medical patients over a long period of time). In addition, the patient monitoring devices may be interconnected via a local network and exchange such data. Clinicians may then have the ability to obtain the physiological parameters even when stationed remotely (e.g., another floor of a hospital, in a building outside a hospital, in a different city, etc.), increasing the quality of medical care provided to patients.

However, the medical care given to patients may be adversely affected if the patient monitoring devices or the systems that support the patient monitoring devices (e.g., a physiological monitoring system) fail (e.g., due to user error, power failure, etc.). While a clinician may detect a failure once it has occurred, the clinician must then identify and notify the appropriate technician. It could take hours to days before a technician can arrive and resolve the issue. Because clinicians and patients may be relying on the physiological parameters to treat ailments, such delay may be unacceptable.

SUMMARY

In order to prevent or reduce the likelihood of a lapse in medical care, it may be beneficial to have the ability to monitor patient monitoring devices or the systems that support the patient monitoring devices. As described above, patient monitoring devices may process and exchange a large amount of data. The processing and exchanging of a large amount of data may cause network communications to become congested (e.g., thereby reducing a data transfer rate and/or preventing data from being transferred), devices to hang, crash, or otherwise become non-responsive, processors to overload (e.g., exceed their processing capabilities), and/or similar ailments. By having the ability to monitor patient monitoring devices or the systems that support the patient monitoring devices, such issues may be identified or predicted to occur. The issues may then be resolved before they result in a lapse in medical care.

As described herein, a system can be constructed to monitor patient monitoring devices or the systems that support the patient monitoring devices, identify issues that are occurring or predict issues that will occur, and resolve such issues. The system may couple to the patient monitoring devices or the systems that support the patient monitoring devices via a network. The system gathers metrics from the patient monitoring devices or the systems that support the patient monitoring devices on a periodic basis. The metrics may be parameters, values, and/or other data that cast a light on the overall health of the patient monitoring devices or the systems that support the patient monitoring devices. For example, the metrics could include processor utilization, memory utilization, network traffic congestion levels, and/or the like. The metrics that can be used by the system are described in greater detail below. Based on an analysis of the metrics, the system determines if there is currently an issue or predicts if an issue will occur with a patient monitoring device or the systems that support the patient monitoring devices. If an issue is identified or predicted, the system may notify the appropriate party (e.g., a clinician, a technician, etc.) so that the issue may be resolved in a timely manner.

Various devices, systems and methods for monitoring physiological monitoring systems are described herein. A method for identifying system performance issue in the physiological monitoring system includes, as implemented by one or more computer systems comprising computer hardware and memory, the one or more computer systems configured with specific executable instructions, receiving, from the physiological monitoring system, first data based on a snapshot taken of a status of the physiological monitoring system at a first time. In an embodiment, the status of the physiological monitoring system comprises at least one indicator of a clinical and/or system performance of the physiological monitoring system. The method can further include comparing, by a processor, the first data with a baseline associated with the physiological monitoring system. The method can further include generating, by the processor, a notification if the first data deviates from the baseline by a predetermined amount. The method can further include transmitting the notification to a system performance monitor.

In certain embodiments, a communication interface module can be configured to receive from a physiological monitoring system first data based on a snapshot taken of a status of the physiological monitoring system at a first time. In an embodiment, the status of the physiological monitoring system comprises at least one indicator of a clinical and/or system performance of the physiological monitoring system. A memory module can be configured to store the first data and a baseline associated with the physiological monitoring system. A processor module can be configured to compare the first data with the baseline associated with the physiological monitoring system and to generate a notification if the first data deviates from the baseline by a predetermined amount. A display module can be configured to display a physical location of a plurality of physiological monitoring systems. In an embodiment, the display module can display the notification and indicate the physiological monitoring system for which the notification is generated.

BRIEF DESCRIPTION OF THE DRAWINGS

Various embodiments will be described hereinafter with reference to the accompanying drawings. These embodiments are illustrated and described by example only, and are not intended to limit the scope of the disclosure.

DETAILED DESCRIPTION

In various embodiments, physiological monitoring systems are systems that monitor one or more parameters of a patient's health. Such systems typically include one or more sensors that measure various physiological signals generated by a medical patient and process the signals to determine any of a variety of physiological parameters. For example, in some cases, a physiological monitoring system can determine any of a variety of physiological parameters of a patient, such as a cardiovascular parameter, a respiratory parameter, an electrical, temperature, chemical, hormonal or other parameter. In some embodiments, the physiological monitoring system monitors a respiratory parameter of the patient, such as: respiratory rate, inspiratory time, expiratory time, i:e ratio (e.g., inspiration-to-expiration ratio), inspiratory flow, expiratory flow, tidal volume, minute volume, apnea duration, breath sounds, rales, rhonchi, stridor, and changes in breath sounds such as decreased volume or change in airflow. In some cases the physiological monitoring system includes an acoustic sensor that detects these or other physiological sounds, such as heart rate, heart sounds (e.g., S1, S2, S3, S4, and murmurs, etc.), changes in heart sounds such as normal to murmur, or split heart sounds indicating fluid overload. The monitoring system can monitor a patient's blood oxygen concentration (e.g., SpO2), or any other blood constituent (e.g., hemoglobin, CO, methemoglobin, etc.). The monitoring system can monitor an electrical parameter of the patient, such as the EKG, EEG, as well. Any of a variety of sensors and monitoring technologies may be included with or provided in communication with such a physiological monitoring system.

A physiological monitoring system of certain embodiments includes one or more patient monitoring devices connected to a shared network using open architecture communications standards. The patient monitoring devices of certain embodiments include a physiological monitor coupled with a network interface module. The physiological monitor includes one or more sensors and a sensor processing module for processing signals from the sensors. The network interface module receives physiological information from the sensor processing module and transmits this information over the shared network. The network interface module may connect to a variety of physiological monitors. In addition, the network interface module of various implementations is a portable bedside device assigned exclusively to one medical patient.

In certain embodiments, the network interface module facilitates establishing a network connection directly with end users over the shared network. These end users, including doctors, nurses, and other hospital staff, may receive physiological information, alarms, and alerts from the network interface module on an electronic device, such as a pager, PDA, laptop, computer, computer on wheels (COW), or the like.

Figure 1:
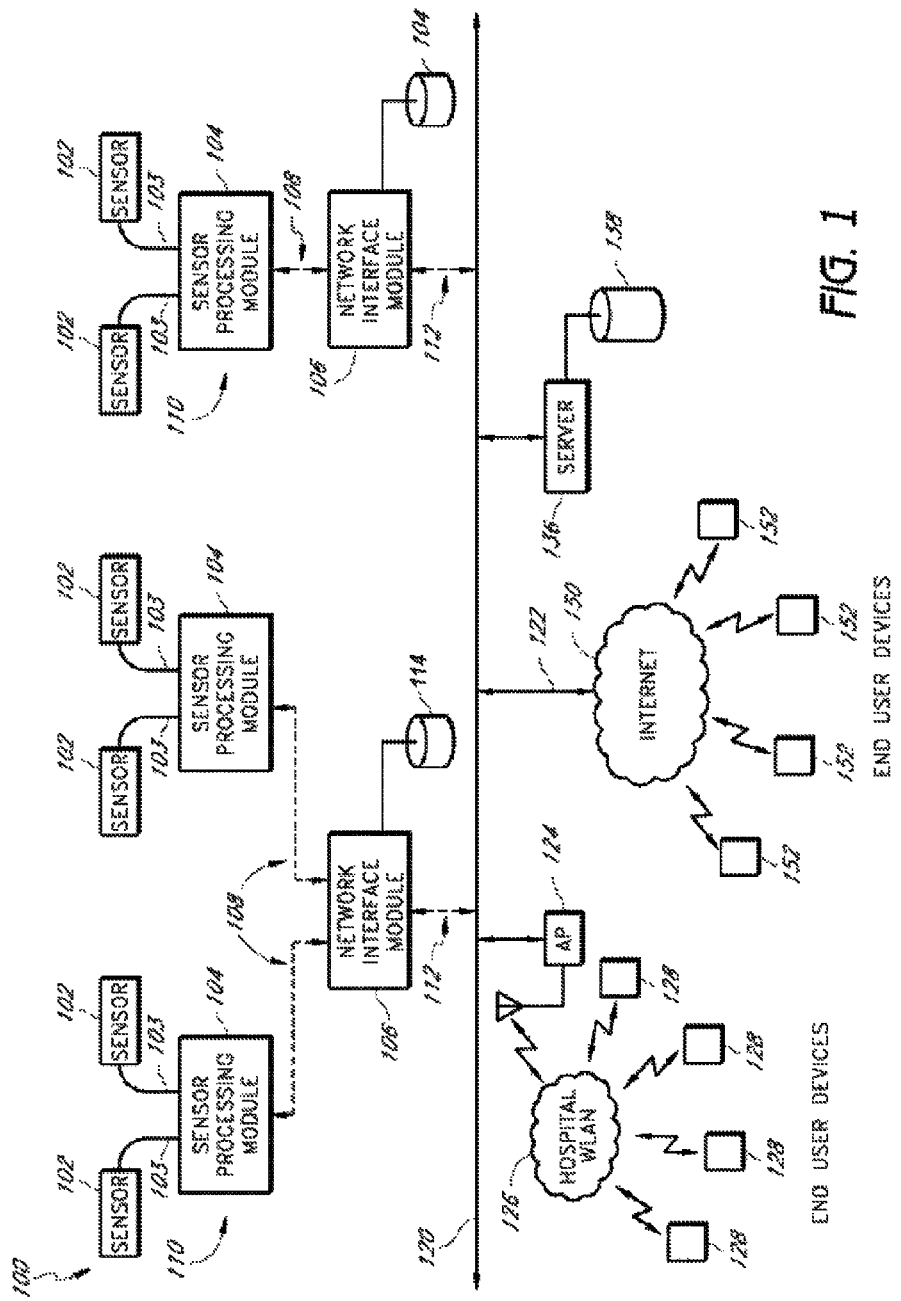
FIG. 1 is an exemplary block diagram showing a physiological monitoring system according to an embodiment of the present invention.

Referring to FIG. 1, certain embodiments of a physiological monitoring system 100 (e.g., alarm notification system) include an open network architecture using "off-the-shelf" hardware and communication protocols. This architecture in various implementations is a shared, or open, network includes multiple patient monitoring devices 110, a network bus 120 (e.g., an Ethernet backbone), and a hospital WLAN 126. In addition, the shared network may further include a connection 122 to an external network, such as the Internet 150, to end user devices 152 over the Internet 150, and to end user devices 128 over the hospital WLAN 126. The physiological monitoring system 100 of certain embodiments is therefore an enterprise system that achieves a cost-effective replacement for currently available patient monitoring systems.

The physiological monitoring system 100 includes a plurality of bedside devices, e.g., patient monitoring devices 110. The patient monitoring devices 110 of various embodiments include sensors 102, one or more sensor processing modules 104, and a communications module, e.g., network interface module 106. In the depicted embodiment, two patient monitoring devices 110 are shown. One patient monitoring device includes one set of sensors 102, one sensor processing module 104, and one network interface module 106. The other patient monitoring device 110 includes two sets of sensors 102, two sensor processing modules 104, and one network interface module 106.

In certain embodiments, each patient monitoring device 110 is used by one medical patient. The patient monitoring devices 110 form a network of patient monitoring devices 110, each of which can communicate with clinicians and other end users over a shared network, including a hospital network 126 and network interfaces to the Internet 150.

One or more sensors 102 of the patient monitoring device 110 are attached to a medical patient. These sensors 102 may include ECG sensors, acoustic sensors, pulse oximeters, and other types of sensors. The sensors 102 obtain physiological information from a medical patient and transmit this information to the sensor processing module 104 through cables 103 or through a wireless connection (not shown). In certain embodiments, the physiological information includes one or more physiological parameters or values and waveforms corresponding to the physiological parameters.

The sensor processing module 104 receives physiological information from the sensors 102. The sensor processing module 104 of certain embodiments includes a circuit having a processor, input ports for receiving the physiological information, software for processing the physiological information in the processor, an optional display, and optionally an input device (e.g., a keyboard). In addition, the sensor processing module 104 contains one or more output ports, such as serial ports. For example, an RS232, RS423, or autobaud RS232 (serial interface standard) port or a universal serial bus (USB) port may be included in the sensor processing module 104.

In certain embodiments, the sensor processing module 104 generates waveforms from signals received from the sensors 102. The sensor processing module 104 may also analyze single or multiparameter trends to provide early warning alerts to clinicians prior to an alarm event. In addition, the sensor processing module 104 in certain embodiments generates alarms in response to physiological parameters exceeding certain safe thresholds.

Example alerts include no communication with pulse oximeter, alarm silenced on pulse oximeter, instrument low battery (pulse oximeter), and transmitter low battery. Example alarms include $SpO_2$ levels and alarms, high and low $SpO_2$, high and low PR, HbCO level and alarms, HbMET level and alarms, pulse rate and alarms, no sensor, sensor off patient, sensor error, low perfusion index, low signal quality, HbCO, HbMET, PI trend alarm, and desat index alarm.

The network interface module 106 in the depicted embodiment is connected to one or more sensor processing modules 104 through one or more connectors 108, which may be serial connectors corresponding to the serial ports in the sensor processing modules 104. Dashed lines on the connector 108 indicate that the network interface module 106 of certain embodiments is not permanently attached to the sensor processing modules 104. In alternative embodiments (not shown), however, the network interface module 106 is contained within a sensor processing module 104.

The network interface module 106 in various implementations includes a processor, an input port (such as a standard RS232 serial port), a network output port such as an Ethernet port, and software which enables the network interface module 106 to act as a network-communications enabled device. In addition, the network interface module 106 includes a storage device 114, which may be included within the network interface module 106 or attached separately to the network interface module 106.

The network interface module 106 manages the connectivity overhead for initiating and maintain connectivity with end user devices over the shared network. In certain embodiments, the network interface module 106 manages connectivity by acting as a microserver or web server. In such instances, the network interface module 106 is a network connection enabled device. As a web server, the network interface module 106 establishes direct connections to the Internet 150, such that an end user may access web pages stored on the storage device 114 of the network interface module 106. In one embodiment, the network interface module 106 therefore does not require a separate server for connecting to the Internet 150. In one embodiment, the network interface module 106 connects to the Internet 150 directly through a modem, such that the connection 122 includes a modem. In managing connectivity over the shared network, the network interface module 106 may also perform security management functions, such as user authentication.

In certain embodiments, the network interface module 106 sends data over the shared network through an access point 124 or other wireless or wired transmitter. Alternatively, the network interface module 106 may communicate physiological information directly to end users over the Internet 150. End users such as clinicians carrying notifier devices, e.g., end user devices 128, 152 connected to the hospital WLAN 126 may receive real-time viewing of physiological patient parameters and waveforms on demand or in the event of an alarm or alert. Real-time or slightly delayed transmission of physiological information in certain embodiments comports with standards for alarm latency in compliance with Joint Commission on Accreditation of Healthcare Organizations (JCAHO) standards for effective alarm response. The network interface module 106 of certain embodiments therefore adds functionality equivalent to a central nurses' station.

In certain embodiments, the network interface module 106 performs context management. In one embodiment, context management includes associating context information with physiological information to form a contextual data package. Context information may include several categories of information, including the categories of context information related to the network interface module 106, context information related to the medical patient, context information related to usage of the network interface module 106, and context information related to a network connection. Within one or more of these context categories, context information might include a patient name, a patients' unique hospital identification number, patient location, an identification number for a network interface module 106, time stamps for events occurring in the physiological monitoring system 100, environmental conditions such as changes to the state of the network and usage statistics of the network interface module 106, and identification information corresponding to the network link (e.g., whether the network connection is WiFi or Ethernet). In one embodiment, the context information in the contextual data package may include all of or any subset of context information from one or more of the context categories.

The network interface module 106 receives context information, for example, by a nurse entering the information in the network interface module 106 or from a server 136. In one embodiment, by receiving this information (including, e.g., patient identification number and location), the network interface module 106 becomes exclusively assigned to the medical patient. The network interface module 106 transmits or communicates the contextual data package to clinicians during an alarm or alert, upon clinician request, or on a scheduled basis. In addition, the network interface module 106 may transmit a continuous stream of physiological information to clinicians.

By optionally connecting to multiple sensor processing modules 104 in certain embodiments, the network interface module 106 is able to associate patient context information and other context information with multiple sensor processing modules 104. Consequently, context can be created for one or more sensor processing modules 104 in addition to context being created for the network interface module 106.

In addition to transmitting the contextual data package, the network interface module 106 in one embodiment stores the contextual data package in the storage device 114. The storage device 114 may be a flash memory, a hard disk drive, or other form of non-volatile or volatile memory. In certain embodiments the storage device 114 acts as a flow control buffer. The network interface module 106 uses the storage device 114 acting as a flow control buffer to perform flow control during communications.

In some implementations, a server 136 may optionally be included in the physiological monitoring system 100. The server 136 in these implementations is generally a computing device such as a blade server or the like. In certain embodiments, the server 136 is an appliance server housed in a data closet. In other embodiments, the server 136 is a server located at a central nurses' station, such as a workstation server.

The server 136 receives contextual data packages from a plurality of network interface modules 106 and stores the contextual data package in a storage device 138. In certain embodiments, this storage device 138 therefore archives long-term patient data. This patient data may be maintained even after the patient is discharged. In storing patient data, the server 136 may act as an interface between the shared network and an external electronic medical record (EMR) system.

The server 136 may also store data concerning user interactions with the system and system performance metrics. Integrated into the server 136 of certain embodiments is a journal database that stores every alert and alarm or a subset of the alerts and alarms as well as human interaction in much the same way as an aviation "black box" records cockpit activity. The journal is not normally accessible to the clinical end user and, without technical authorization, cannot be tampered with. In addition, the server 136 may perform internal journaling of system performance metrics such as overall system uptime.

In one embodiment, the journaling function of the server 136 constitutes a transaction-based architecture. Certain transactions of the physiological monitoring system 100 are journaled such that a timeline of recorded events may later be re-constructed to evaluate the quality of healthcare given and/or to evaluate the performance of the physiological monitoring system 100. These transactions include state changes relating to physiological information from the patient monitoring devices 100, to the patient monitoring devices 110, to the hospital WLAN 126 connection, to user operation, and to system behavior. Journaling related to the physiological information received from a physiological monitor in one embodiment includes recording the physiological information itself, recording changes in the physiological information, or both.

The server 136 in certain embodiments provides logic and management tools to maintain connectivity between network interface modules 106, clinician notification devices such as PDAs and pagers, and external systems such as EMRs. The server 136 of certain embodiments also provides a web based interface to allow installation (provisioning) of software rated to the physiological monitoring system 100, adding new devices to the system, assigning notifiers (e.g., PDAs, pagers, and the like) to individual clinicians for alarm notification at beginning and end of shift, escalation algorithms in cases where a primary caregiver does not respond to an alarm, interfaces to provide management reporting on the alarm occurrence and response time, location management, and internal journaling of system performance metrics such as overall system uptime (see, e.g., FIG. 3 and accompanying description).

The server 136 in certain embodiments also provides a platform for advanced rules engines and signal processing algorithms that provide early alerts in anticipation of a clinical alarm. The operating system on the server 136 in one embodiment is Linux-based for cost reasons, though a Microsoft-based or other operating system may also be used. Moreover, the server 136 is expandable to include data storage devices and system redundancy capabilities such as RAID (random array of independent disks) and High Availability options.

In another embodiment (not shown), end user devices 128, 152 include one way POC SAG Pagers having a 2 line display with audible and vibrate mode, of suitable size and durability for severe mechanical environments typical of hospital general floor settings. In yet another embodiment, the end user devices 128, 152 include two way paging systems, such as Motorola Flex and WLAN pagers. One advantage of two-way paging is the ability to confirm message receipt and the ability to remotely silence alarms. Wireless PDAs may also be used by end users based on ruggedness and acceptable form factors as determined by an end user. An example of such a device is the Symbol Technology MC50 PDA/Barcode Scanner.

Figure 2:
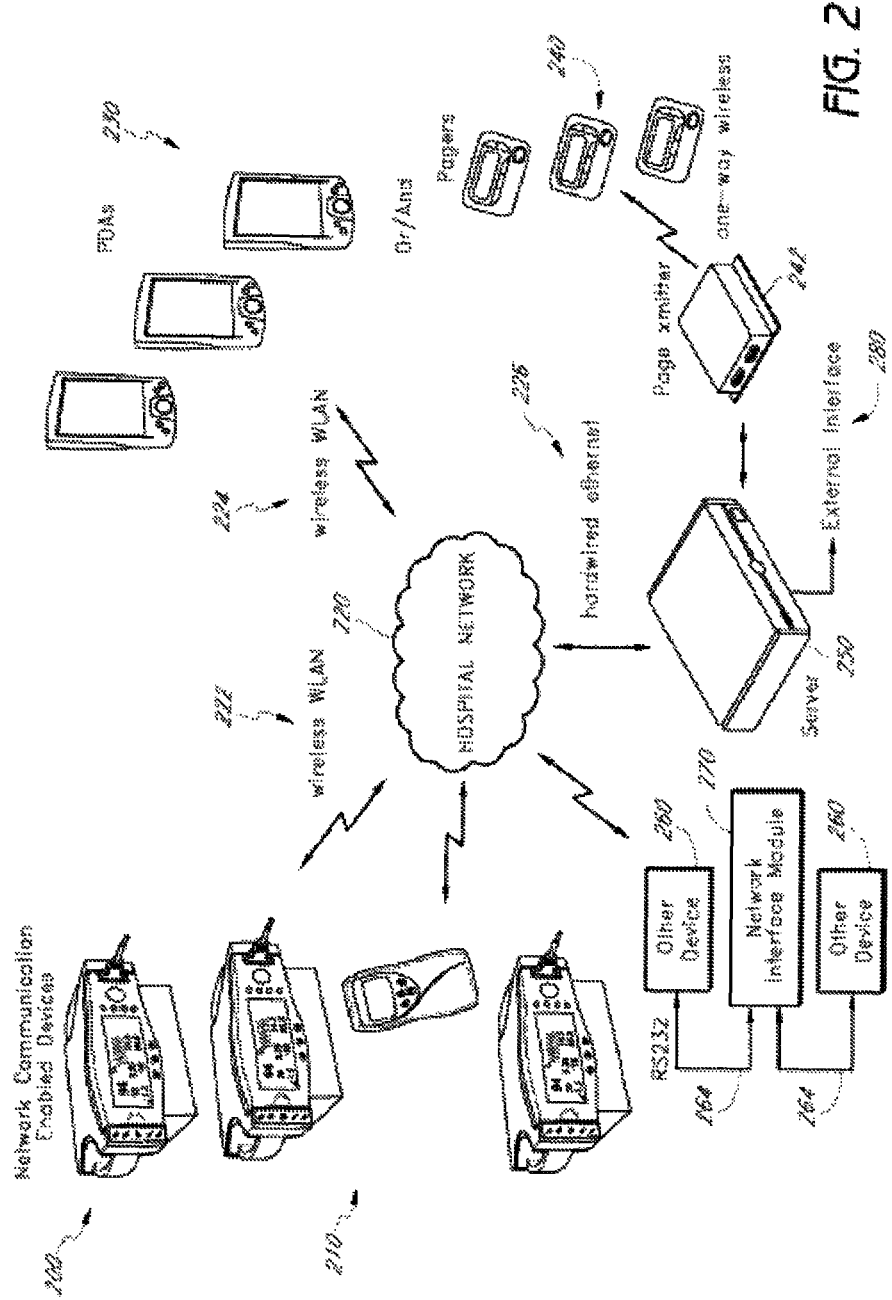
FIG. 2 is an exemplary block diagram showing another embodiment of a physiological monitoring system.

FIG. 2 depicts another embodiment of the physiological monitoring system 200 of the present invention. The physiological monitoring system 200 includes network communications enabled devices 210. The network communications enabled devices 210 are connected directly to a hospital network 220 through a wireless connection. In certain embodiments, the network communications enabled devices 210 include sensors and sensor processing modules, similar to the sensors 102 and sensor processing modules 104 of FIG. 1. Certain of these network communications enabled devices 210 are bedside devices, and others are handheld or otherwise patient-worn devices that may be used by an ambulatory (mobile) patient.

The hospital network 220 transmits physiological information and context information to clinician notifier devices, including pagers 240, PDAs 230, and the like. In certain embodiments, the hospital network 220 utilizes a server 250 to transmit contextual data packages to a page transmitter 242, which further transmits the data to one-way wireless pagers 240. An external interface 280 may be coupled with the server 250. The external interface 280 could include one or more of the following: enterprise paging, nurse call systems, wide area paging systems, enterprise clinical and patient information systems, and third party monitoring and surveillance systems.

Certain other devices 260, such as some patient monitoring equipment, are not network communications enabled devices. That is, these other devices 260 are unable to connect to a network unaided. In the depicted physiological monitoring system 200, example devices 260 that are not network communications enabled are connected to a network interface module 270. The network interface module 270 is connected to the non-network communication enabled other devices 260 through RS232 cables 264. Such a connection is a standardized serial connection found on many devices. Because the network interface module 270 has an RS232 port, the network interface module 270 can allow non-network communication enabled patient monitoring devices to connect directly to the hospital network 220 and also to the Internet.

Moreover, by connecting to one or more other devices 260 in some embodiments, the network interface module 270 is able to associate patient context information and other context information with one or more other devices 260. Consequently, context can be created for one or more other devices 260 in addition to context being created for the network interface module 270.

Figure 3:
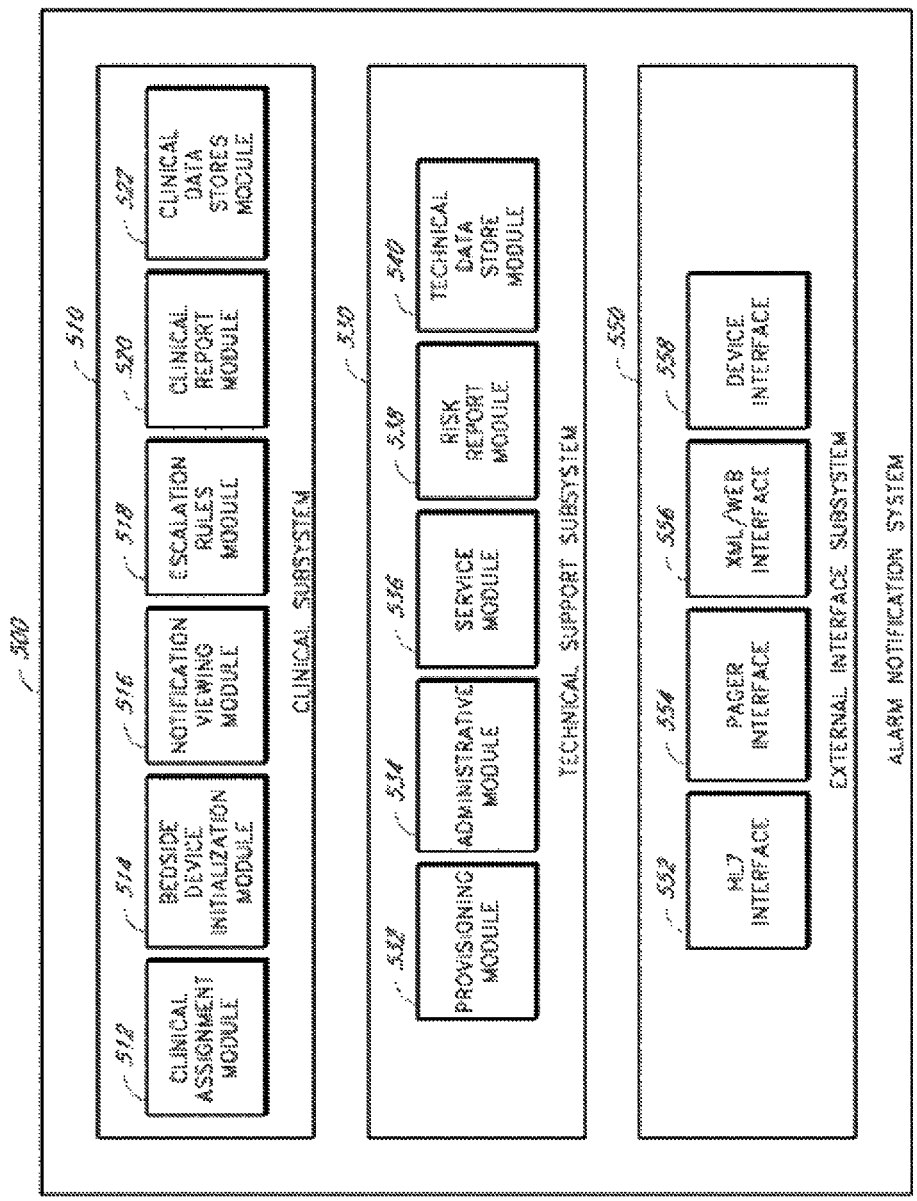
FIG. 3 is an exemplary block diagram showing an alarm notification system according to an embodiment of the present invention.

FIG. 3 depicts an alarm notification system 500 in accordance with certain embodiments of the present invention. A clinical subsystem 510 defines the major software components of alarm notification system 500 including a clinical assignment module 512, a bedside device initialization module 514, a notification and viewing module 516, an escalation rules module 518, a clinical report module 520, and a clinical data stores module 522. An authentication feature is built into mobile computing devices in compliance with HIPAA and hospital IT policies.

The clinical assignment module 512 has an assignment function. A nursing supervisor assigns individual nurses to specific patients at the start of each shift and upon admission of new patients. Shift assignments take place at change of shift during a "report" transition exercise where individual nurses and nursing supervisor from previous shift "hand off" patients to the next shift. The report can be either formal where all nurses attend or informal dependent on hospital nursing service policies and procedures. The clinical assignment module 512 provides an intuitive interface that allows a listing of available nurses to be assigned individual patients. The major user of this module is the unit clerk as assigned by the nursing supervisor. A nurse can be assigned one or more patients or all patients. An alternative work flow is self assignment where individual nurses assign patients themselves in which case they perform functions of the unit clerk. In the self assignment model, a default is implemented where any unassigned patient is either assigned to all nurses or the nursing supervisor.

The bedside device initialization module 514 has bedside devices, such as the network interface modules described above, that are sometimes set up by an aide to the nurse. In the case where the nurse performs this task, she or he performs the functions of the nursing aide. Work flow includes delivering a device to bedside, applying sensors, initializing the device, and setting patient context, such as name, ID and location.

The notification and viewing module 516 assigns a wireless notification device, such as a one-way pager, PDA, IP telephone, COW, or Tablet to individual nurses. The device becomes associated with her or him. Alarms are routed to the notification device based on the clinical assignment module 512. Non-dedicated notifier solutions such as hospital owned paging systems issued to nurses have unknown latency characteristics. A general purpose interface is available at the server with a latency of less than 1 second upon receipt from the bedside device and is time stamped upon presentation to the server external interface and stored in a journaling system within the server. An additional interface for mobile computing platforms such as PDA, COWS, and Tablets allows viewing of current and trend data for an individual patient.

The escalation rules module 518 has a rules engine that actuates an escalation policy defined by the hospital. The escalation rules module 518 provides alternative routing of alarms to alternative and additional clinical users in the event an alarm is not responded to or persists for a predefined (e.g., by a policy) period of time. The escalation rules module 518 in certain embodiments routes alarms to an emergency response team.

The clinical report module 520 provides predefined formatted reports on the clinical data from which to determine physiologic condition and/or progress. More than one report may be dependent on end user needs. Reports are not time critical views of individual patients and may be remotely viewed by clinicians who have alarm notification system 500 privileges and have been authenticated by the alarm notification system 500. These reports are web browser views that allow clinicians to set viewing parameters such as time and parameter scales and alarm review.

The clinical data stores module 522 provides data storage and database resources to store information as known to those skilled in the art.

Further shown in FIG. 3, a technical support subsystem 530 is isolated from the clinical subsystem 510 in compliance with HIPAA and as such does not allow viewing or access to any patient information with the exception of the risk report module 538. The technical support subsystem 530 includes a provisioning module 532, an administration module, a service module 536, a risk report module 538, and a technical data store module 540.

The provisioning module 532 provides provisioning, which is the initial installation of the system and first customer use. The primary user of the provisioning module 532 is the field installer. The provisioning module 532 contains all the start up scripts and system configurations to bring the system from shipping boxes to full alarm notification system 500 functionality. Provisioning includes steps to configure individual devices, notifiers such as pagers, PDA, COW, Tables and IP telephone at the customer site, preferably by wireless means (e.g., Bluetooth).

The administrative module 534 provides a system interface for the application administrator to set up users, set policies for various actor privileges such as a nurse's aide being able to set or change alarms, set up allowed device connection identifications, and other general systems administrative duties typical of IT systems.

The service module 536 provides interfaces for various technical support actors including remote service, IT Service, and Biomed Service. Each of these actors may perform each other's functions. Interfaces allow the service actors to access system performance data to access performance, for example, data traffic, device assets connected, software version management, CPU loading, network loading, etc. and execute remote technical service procedures, for example, resetting a printer queue, repartition of disk, uploading software patches, etc. The service module 536 includes a full journaling function that stores every user interaction or a portion of user actions that can be captured by the system, especially changes in default values or alarm settings.

The risk report module 538 provides summary reports on alarm occurrences, duration of alarm, clinical response time to alarms and other statistical data to determine overall effectiveness of clinical response to alarms in compliance with JCAHO, other regulatory bodies, and internal quality assurance committees.

The technical data stores module 540 has the same characteristics as the clinical data stores module 522 except that the technical data stores module 540 is used for technical data. The technical data stores module 540 may or may not share the same physical and logical entity as the clinical data stores module 522.

Additionally shown in FIG. 3, an external interface subsystem 550 provides interfaces to bedside devices and external systems such as electronic medical records, admit discharge, transfer systems, POCSAG pager systems, middleware engines such as Emergin, and Web/XML, enabled devices such as wireless PDAs, COWs and Tablet PCs. The external interface subsystem 550 has an HL7 interface 552, a pager interface 554, an XML/Web interface 556, and a device interface 558.

The HL7 interface 552 provides a bi-directional interface to electronic medical records (EMR) and supports both push and pull models. The push model is when a bedside nurse initiates data transfer. The pull model is when an EMR system polls the alarm notification system 500 server. The pager interface 554 provides output to external paging system. Message latency is identified to an end user for any user-owned paging solution. This same output can be used for middleware alarm notification systems such as Emergin. The XML/Web interface 556 provides bi-directional interface with mobile computing platforms such as wireless PDA, COWs, Tables, and Web-enabled IP phones. Mobile computing platforms support Web Browser XML applications. The device interface 558 provides a bi-directional interface to bedside devices as well as to other devices enabled by the communications module or accessory. Application Programmer Interface (API) capability is an option for interfacing to other bedside devices.

The major end users of the alarm notification system 500 system (not shown or described for simplicity) include hospital electronic medical records, admit discharge transfer, pharmacy, clinical information, patient flow tracking and others. Actors, e.g., users of the alarm notification system 500, including clinical actors and technical support actors. The clinical actors include nursing supervisors, unit clerks, nursing aides, nurses, rapid response teams and respiratory therapists.

A nursing supervisor assigns individual nurses to specific patients at the beginning of each shift. Shift can vary according to hospital staffing policies. A unit clerk takes direction from the nursing supervisor, typically inputs assignments into system and monitors overall system. A unit clerk may not be available for all shifts. A nursing aide takes assignments from nurse or nursing supervisor, typically applies bedside device sensor, initializes the bedside device and sets alarms to default values. A nurse has primary responsibility for individual patient care and primary response to alarms. The nurse is assigned by nursing supervisor to more than one patient dependent on her/his skills and patient needs and is not always assigned the same patient. Nursing aides are not found in all hospitals.

A rapid response team responds to clinical emergencies initiated by either a bedside nurse or a nursing supervisor. The team supports more than one care unit and has one or more members depending on shift. Rapid Response Teams may not be implemented in all hospitals. A respiratory therapist has responsibilities for management of respiratory care for more than one patient and usually more than one care unit. Respiratory therapists are not found in some international settings.

Clinical actor performance substitution allows a high capability actor to assume the roles of other actors. Alarm notification system 500 allows mechanisms for such performance. For example, a nursing supervisor may perform functions of a unit clerk nursing aide, a nurse and a rapid response team. A nurse may perform functions of a unit clerk, a nursing aide and a rapid response team. In some international markets a nurse may perform the functions of a respiratory therapist.

The technical support actors include field installers, application administrators, remote services, IT engineers, biomedical engineers and risk managers. A field installer provisions the system for initial installation, installs components, and validates that the installation and configuration meet a purchasing contract. An application administrator sets up and maintains user accounts and systems defaults. A remote service provides remote diagnostics and system maintenance over a remote link, such as dial up and VPN. An IT engineer provides network support services if the system is integrated with the hospital IT network. A biomedical engineer provides bedside and system primary service. A risk manager reviews reports for quality and risk mitigation purposes. Technical support actors may also fill in for other actors. For example, an IT engineer, a biomedical engineer, or a remote service can perform the functions of an application administrator. An IT engineer or a biomedical engineer can perform each other's functions.

In certain embodiments, systems and methods are provided for rapidly storing and acquiring physiological trend data. For instance, physiological information obtained from a medical patient can be stored in a round-robin database. The round-robin database can store the physiological information in a series of records equally spaced in time. Parameter descriptors may be used to identify parameter values in the records. The parameter values can be dynamically updated by changing the parameter descriptors to provide for a flexible database. In addition, the size of files used in the database can be dynamically adjusted to account for patient condition.

Additionally, in certain embodiments, medical data obtained from a clinical network of physiological monitors can be stored or journaled in a journal database. The medical data can include device events that occurred in response to clinician interactions with one or more medical devices. The medical event data may also include device-initiated events, such as alarms and the like. The medical data stored in the journal database can be analyzed to derive statistics or metrics, which may be used to improve clinician and/or hospital performance.

Figure 4:
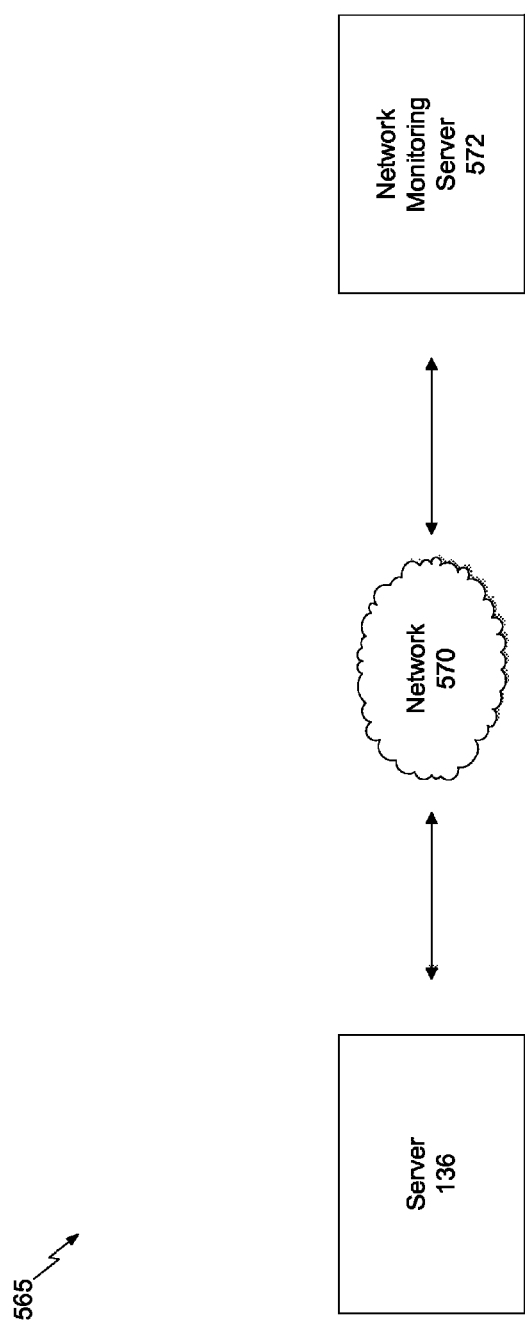
FIG. 4 is a block diagram of a system that may monitor a physiological monitoring system, such as the physiological monitoring system of FIG. 1.

FIG. 4 depicts a block diagram of a system 565 that may monitor a physiological monitoring system, such as the physiological monitoring system 100 described herein with respect to FIG. 1. In certain embodiments, the system 565 comprises a server of the physiological monitoring system 100, such as server 136 described herein with respect to FIG. 1, a network 570, and/or a network monitoring server 572. While FIG. 4 illustrates one network monitoring server 572, this is not meant to be limiting, as the functionality described herein may be implemented in more than one server (e.g., these servers can be co-located or can be geographically separate, etc.). The functionality described herein may also be implemented in one or more virtual machines that execute on a physical server. In addition, the functionality described herein may be implemented in network monitoring server 572 or in other computing devices. Further, the functionality described herein may be implemented in a cloud computing environment.

As described herein, the server 136 may store data concerning user interactions with the system (e.g., clinical performance metrics, such as number of alarms, alarm response times, etc.) and system performance metrics. In certain embodiments, certain transactions of the physiological monitoring system 100 are journaled by the server 136 such that a timeline of recorded events may later be reconstructed to evaluate the quality of healthcare given and/or to evaluate the performance of the physiological monitoring system 100. For example, the server 136 may capture the data concerning user interactions with the system and system performance metrics by taking a snapshot of the physiological monitoring system 100 (e.g., a state of the physiological monitoring system) at a given point in time. The server 136 may capture such data by requesting reports, logs, or the like from various modules within the physiological monitoring system 100 (e.g., the service module 536, the risk report module 538, etc.). The server 136 may also transmit the data concerning user interactions with the system and system performance metrics to the network monitoring server 572 via the network 570. In an embodiment, the server 136 may capture and/or transmit the data in regular intervals, such as every minute, every hour, every day, and/or the like.

The network 570 may include any communications network, such as the Internet 150. Network 570 may be a wired network, a wireless network, or a combination of the two. For example, the network 570 may be a local area network (LAN), a wide area network (WAN), the Internet, and/or combinations of the same.

The network monitoring server 572 may be in communication with any of a variety of information-providing devices, either directly or via the network 570. For example, the network monitoring server 572 may be in communication with one or more servers associated with one or more physiological monitoring systems. In certain embodiments, the network monitoring server 572 may be configured to receive data concerning user interactions with the system and system performance metrics from each physiological monitoring system that it is in communication with. The network monitoring system 572 may also be configured to generate and transmit messages, such as notifications, commands, and/or instructions, to each physiological monitoring system that it is in communication with. In this way, the network monitoring server 572 may be able to identify current and/or future clinical and/or system performance issues and respond appropriately.

Figure 5:
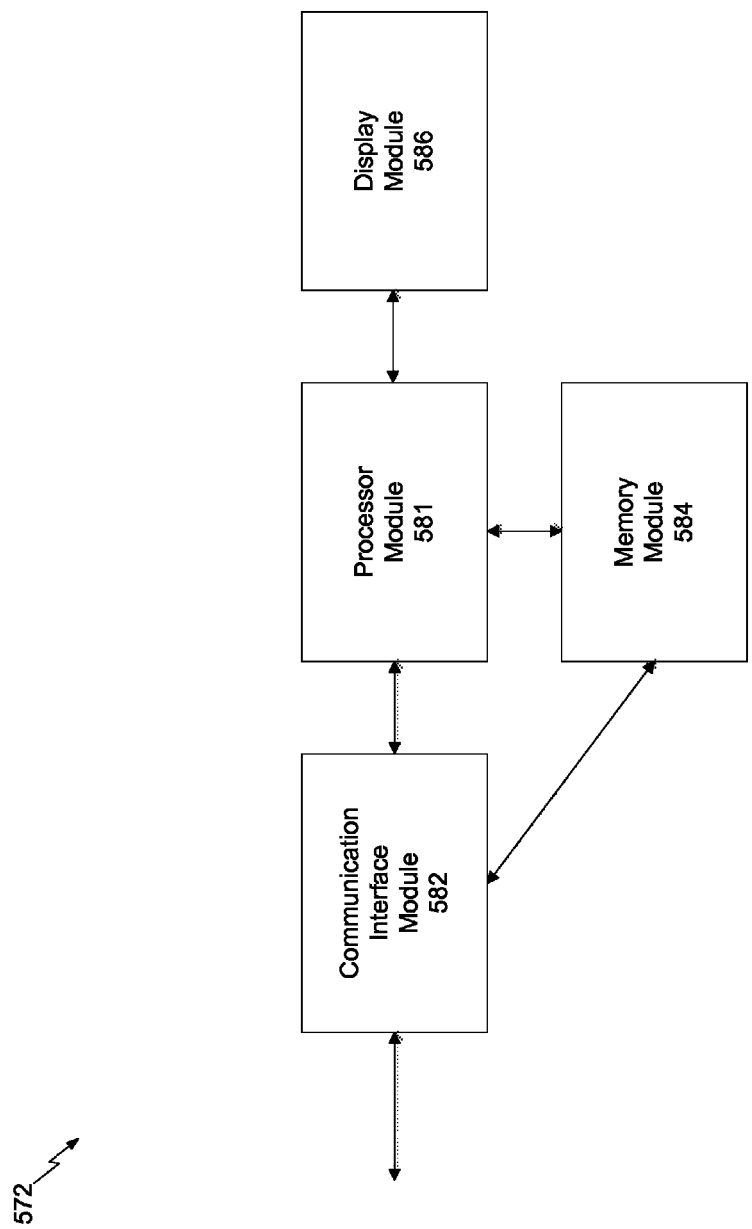
FIG. 5 is a more detailed block diagram of a network monitoring server, such as the network monitoring server of FIG. 4.

FIG. 5 illustrates a more detailed block diagram of a network monitoring server, such as network monitoring server 572 described herein with respect to FIG. 4. The network monitoring server 572 may comprise a communication interface module 582, a processor module 581, a memory module 584, and/or a display module 586.

In certain embodiments, the communication interface module 582 is configured to communicate with the servers associated with physiological monitoring systems, such as server 136. For example, the communication interface module 582 may receive data, such as clinical and/or system performance metrics, from the server 136. The communication interface module 582 may receive the clinical and/or system performance metrics from the server 136 in regular intervals or when such metrics deviate from a baseline (e.g., historical values) as described herein. As an example, clinical and/or system performance metrics may include indicators of clinical and/or system performance, such as processor utilization by the physiological monitoring system 100, memory utilization by the physiological monitoring system 100, a number of times a subsystem (e.g., the clinical subsystem 510, the technical support subsystem 530, and/or the external interface subsystem 550 of the alarm notification system 500) associated with the physiological monitoring system 100 failed, a number of times at least one medical device (e.g., sensor 102, sensor processing module 104, network interface module 106, end user devices 128, end user devices 152, other devices like radios, cameras, or the like, etc.) disconnected from the physiological monitoring system 100, a number of times at least one medical device generated an alarm condition (e.g., when an alarm occurs), a number of errors (e.g., login/credential errors, system driver errors, software errors, etc.) generated by the physiological monitoring system 100, a number of times at least one medical device generated an alarm condition that lasted more than a predetermined amount of time (e.g., several seconds, like three or four, which may indicate that a page was sent to an end user device 128 and/or 152), and a number of times at least one medical device generated an alarm condition that lasted less than the predetermined amount of time (e.g., which may indicate that a page was not sent to an end user device 128 and/or 152). If applicable, the communication interface module 582 may be further configured to receive information identifying and otherwise relating to the medical device(s) and/or other component(s) of the physiological monitoring system 100 that may be causing clinical and/or system performance issues.

The received clinical and/or system performance metrics may be stored in the memory module 584. In certain embodiments, the received data may be aggregated for use by the processor module 581 as described herein. In further embodiments, the memory module 584 may store baseline information associated with each physiological monitoring system that the network monitoring server 572 is in communication with. For example, at or near a first time when the physiological monitoring system and the network monitoring server 572 are in communication, the network monitoring server 572 may receive the clinical and/or system performance metrics from the physiological monitoring system for storage in the memory module 584. After a set number of data points (e.g., data communication sessions between the network monitoring server 572 and the physiological monitoring system occurring at different times) have been received (e.g., 5 data points, 10 data points, etc.), such data points may be aggregated and identified as the baseline clinical and/or system performance metrics associated with the respective physiological monitoring system. This baseline information may represent the clinical and/or system performance metrics that are to be considered normal for the respective physiological monitoring system. Any deviation from this baseline may indicate that there is some issue that is or will be occurring in the respective physiological monitoring system. In other words, identifying any deviation from this baseline may allow the network monitoring server 572 to identify an issue that is occurring or predict an issue that could occur in the future.

In certain embodiments, aggregation may occur by clinical and/or system performance indicators. For example, metrics related to a number of times at least one medical device generated an alarm condition that lasted more than a predetermined amount of time may be aggregated together, metrics related to a number of times at least one medical device generated an alarm condition that lasted less than the predetermined amount of time may be aggregated together, and so on. In further embodiments, aggregation may occur by physiological monitoring system such that metrics from different physiological monitoring systems would not be aggregated together. Each of the metrics may retain their identifying information (e.g., the physiological monitoring system the metric is associated with, a time the metric was captured at the physiological monitoring system, etc.) when aggregated such that aggregated data may yield trends and/or other information if plotted or otherwise visually displayed.

The processor module 581 may be configured to retrieve data from the communication interface module 582 and/or the memory module 584. For example, the processor module 581 may be configured to retrieve clinical and/or system performance metrics from the communication interface module 582 and/or the memory module 584 and/or aggregated data from the memory module 584. The processor module 581 may also be configured to generate baseline information as described herein, and store and retrieve baseline information from the memory module 584. In certain embodiments, the processor module 581 compares a single set of clinical and/or system performance metrics and/or the aggregated data with the baseline information to determine whether there is any deviation from the baseline. Thus, the processor module 581 is configured to determine whether an issue is occurring and/or predict whether an issue will occur in the future based on the comparison.

As described herein, a deviation from the baseline may indicate there is an issue with the clinical and/or system performance within the physiological monitoring system 100. For example, if the baseline information indicates that a normal number of errors generated by the physiological monitoring system 100 during a given period (e.g., an hour, a day, a week, etc.) is 20, then there is or there may be an issue with the clinical and/or system performance within the physiological monitoring system 100 if the aggregated data and/or the received single set of clinical and/or system performance metrics indicates that a number of errors generated by the physiological monitoring system 100 during the same given period deviates from 20 by a predetermined amount (e.g., deviates by a certain percentage, deviates by certain number, etc.).

In certain embodiments, if the processor module 581 determines that there is sufficient deviation from the baseline, the processor module 581 may generate a notification. The processor module 581 can generate the notification at a time or near a time that there is sufficient deviation from the baseline. Alternatively or in addition, the processor module 581 can generate the notification at the end of a periodic interval. The notification may be displayed (e.g., via the display module 586) and/or transmitted to a system performance monitor (e.g., a computing device within the physiological monitoring system 100, an entity that monitors the physiological monitoring system 100, such as the user of the network monitoring server 572, a computing device outside the physiological monitoring system 100, a paging service, a database, etc.) via the communication interface module 582. As an example, a notification may inform a user of the network monitoring server 572 and/or operators of the physiological monitoring system 100 of a medical device(s) and/or other component(s) of the physiological monitoring system 100 that may be causing problems to the system (e.g., that caused the generation of the notification). The notification may also include a command or instructions on how to solve the current or potential issue. In some aspects, such a command or instruction may explain to a user how to solve the current or potential issue. In other aspects, such a command or instruction is executed by a processor or other such device within the physiological monitoring system 100 or the network monitoring server 572 to solve the current or potential (e.g., predicted) issue. For example, the service module 536 may execute such a command or instruction.

The display module 586 may be a display, such as a screen (e.g., an LCD screen, an LED screen, a touch screen, etc.).

In some aspects, the display module 586 may receive inputs, such as touch inputs, from a user. The display module 586 may be configured to display a geographic region and the locations of one or more physiological monitoring systems within the geographic region. The one or more physiological monitoring systems may be represented using any symbol. As described herein, the display module 586 may further be configured to display the notification. For example, when a notification is generated, the display module 586 may display the notification (immediately or after the physiological monitoring system it is associated with is chosen) and/or the physiological monitoring system it is associated with.

In certain embodiments, the physiological monitoring system may be indicated graphically (e.g., via a different color symbol, a flashing symbol, text, etc.) and/or may be selectable by a user. Upon selecting a physiological monitoring system (e.g., by touching, clicking, pressing, hovering over, typing, speaking, etc.), further information may be displayed, such as a single set of clinical and/or system performance metrics and/or aggregated data. In this way, a user associated with the network monitoring server 572 may be able to access and view clinical and system performance metrics for a selected physiological monitoring system. The user may be able to view such metrics to further investigate current and/or potential issues with the physiological monitoring system and/or to identify issues with the physiological monitoring system even if no notification has been generated.

Figure 6A:
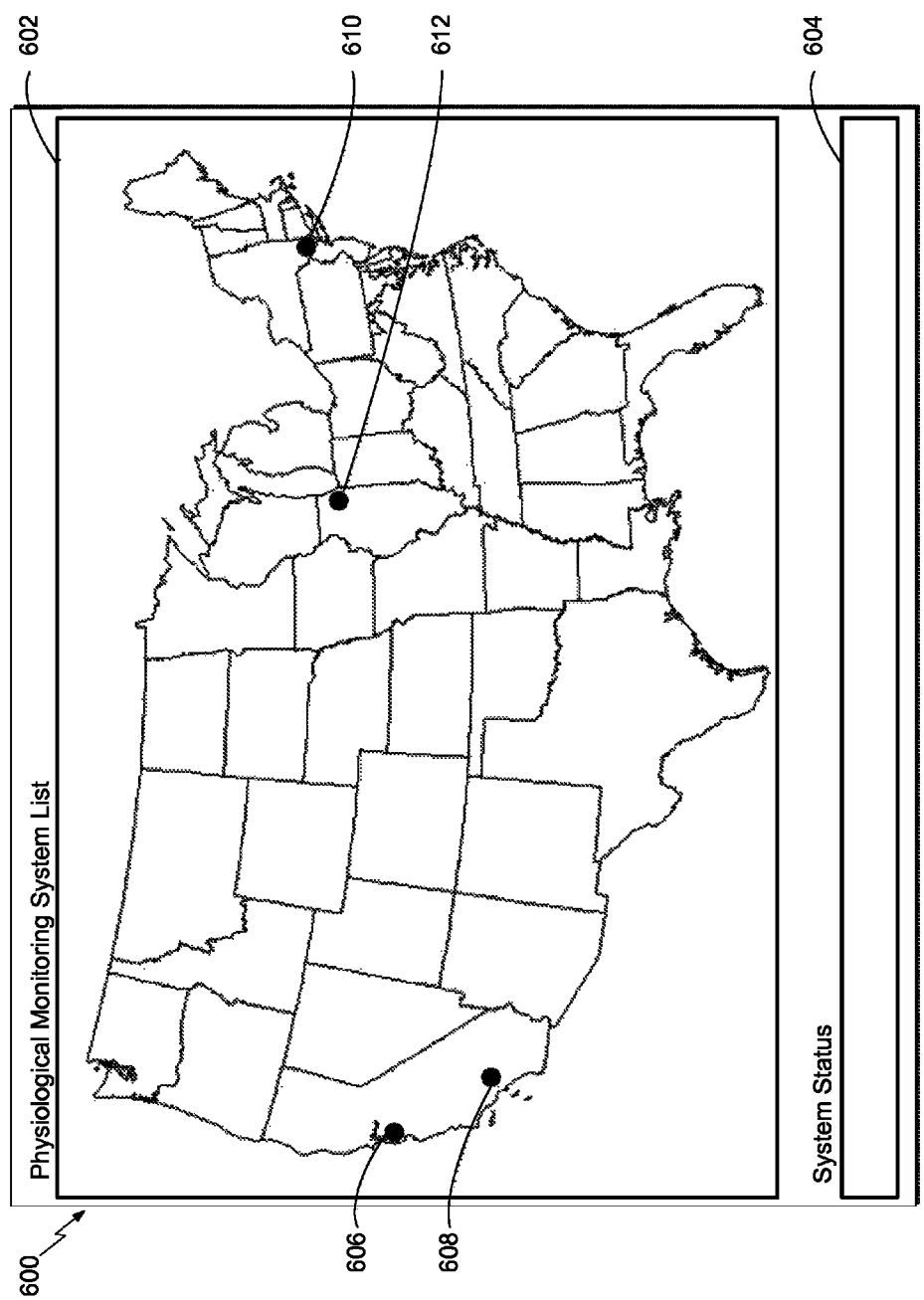
FIGS. 6A-C are a network monitoring screen that may be generated by a display module, such as the display module of FIG. 5.
Figure 6B:
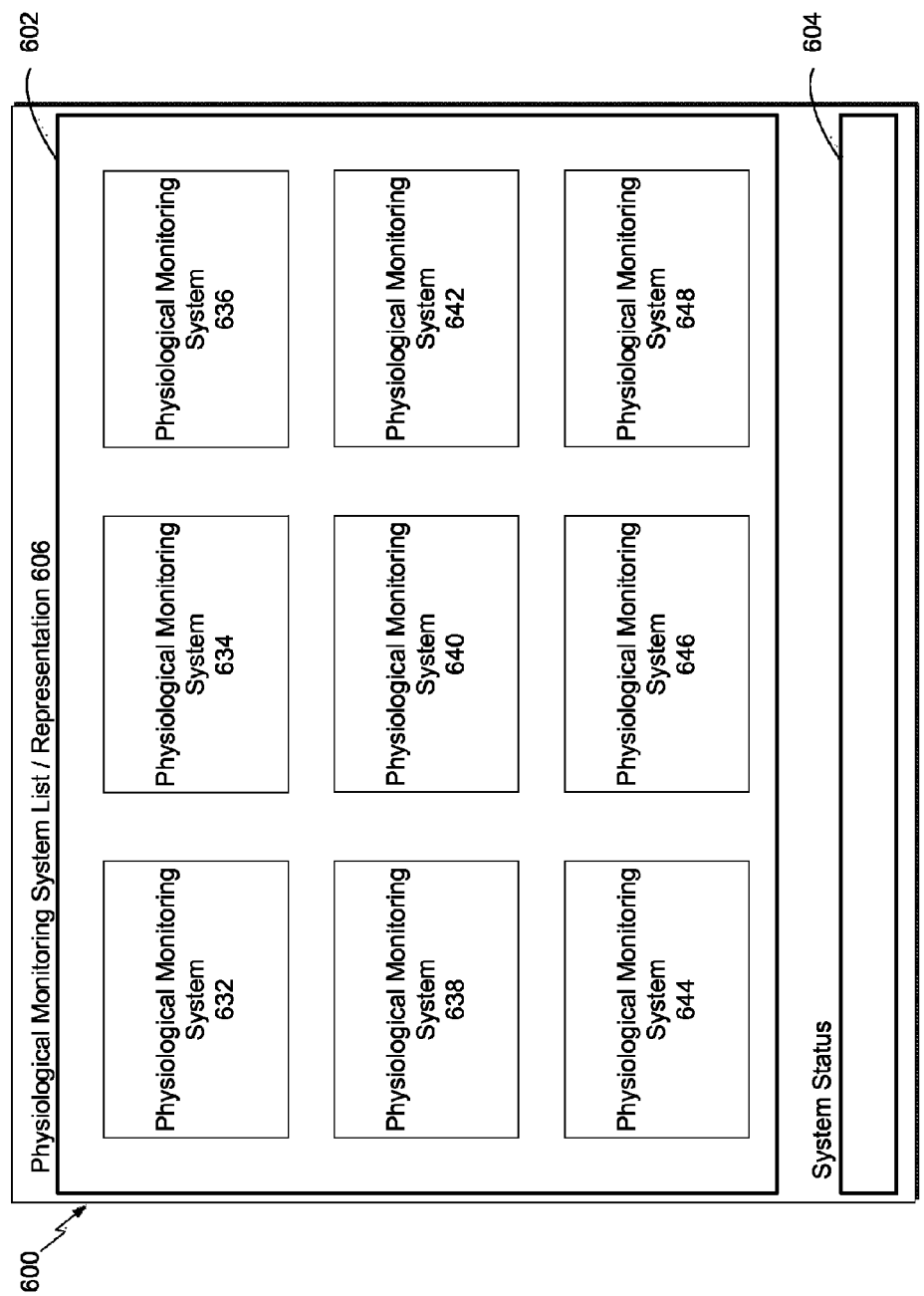
Figure 6C:
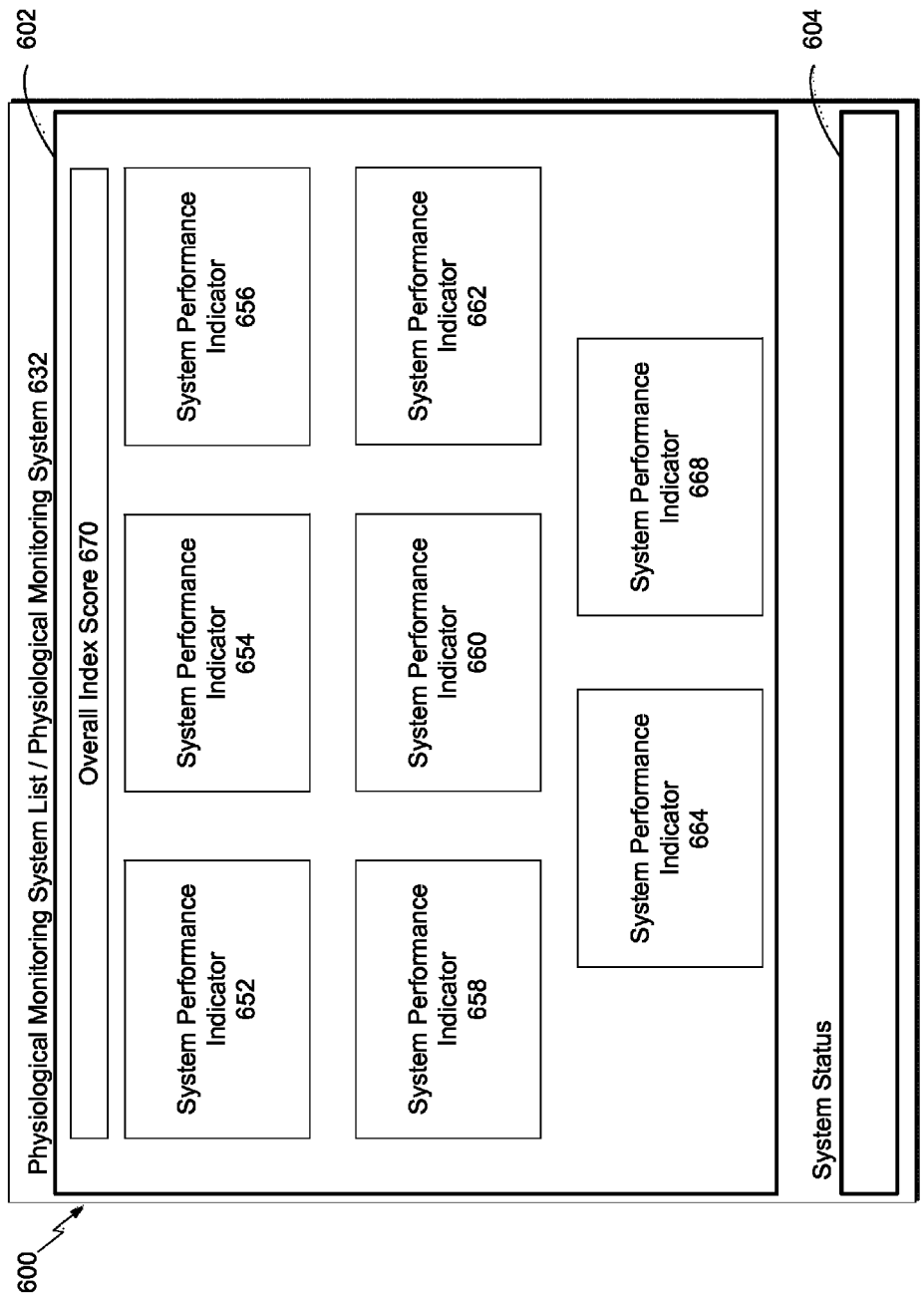

FIGS. 6A-C illustrate a network monitoring screen 600 that may be generated by a display module, such as display module 586 described herein with respect to FIG. 5. In certain embodiments, the network monitoring screen 600 may include a physiological monitoring system list pane 602 and/or a system status pane 604. In other embodiments, not shown, more or less information may be displayed within the network monitoring screen 600 and/or the physiological monitoring system list pane 602 and the system status pane 604 may be combined into one pane.

In certain embodiments, as illustrated in FIG. 6A, the physiological monitoring system list pane 602 includes a geographic region and one or more representations 606, 608, 610, and/or 612 of physiological monitoring systems. In some aspects, one or more representations 606, 608, 610, and/or 612 may represent a plurality of physiological monitoring systems. For example, representation 606 may symbolize the presence of three physiological monitoring systems (e.g., three different hospitals) within the geographic region where the representation 606 is located. As described herein, one or more representations 606, 608, 610, and/or 612 is selectable by a user. For example, a user may touch, press, click, hover over, type, speak, or otherwise choose a representation 606, 608, 610, or 612 and more information may displayed as described herein.

In certain embodiments, the system status pane 604 may display a notification when one is generated by the processor module 581. The system status pane 604 may indicate details of the notification and/or the representation 606, 608, 610, 612 and/or physiological monitoring system the notification is associated with.

In certain embodiments, as illustrated in FIG. 6B, once a representation 606, 608, 610, and/or 612 is selected, further information may be displayed within the physiological monitoring system list pane 602. For example, representation 606 may include 9 different physiological monitoring systems 632, 634, 636, 638, 640, 642, 644, 646, and/or 648. If representation 606 is chosen, representations of one or more of physiological monitoring systems 632, 634, 636, 638, 640, 642, 644, 646, and/or 648 may be displayed within the physiological monitoring system list pane 602. As an example, the representations of the physiological monitoring system 632, 634, 636, 638, 640, 642, 644, 646, and/or 648 may indicate a status of the respective physiological monitoring system. Such a status may be indicated graphically (e.g., via color coding based on whether the system is error free, whether the system is experiencing a few errors, and/or whether it is anticipated the system is or will face issues, etc.), numerically (e.g., index scores described below), or the like. Each of the representations of the physiological monitoring systems 632, 634, 636, 638, 640, 642, 644, 646, and/or 648 may be selectable (by a user) in ways as described herein to provide further information about the selected physiological monitoring system 632, 634, 636, 638, 640, 642, 644, 646, or 648.

As illustrated in FIG. 6C, upon selecting a representation of a physiological monitoring system 632, 634, 636, 638, 640, 642, 644, 646, or 648, the network monitoring screen 600 may display an index score for the chosen physiological monitoring system and/or indicators of clinical and/or system performance for the chosen physiological monitoring system. For example, if the representation of the physiological monitoring system 632 is selected, an overall index score 670 and eight indicators 652, 654, 656, 658, 660, 662, 664, and/or 668 may be displayed. In other embodiments, fewer or more indicators may be displayed.

The overall index score 670 may be a numerical representation of the overall health of the physiological monitoring system 632. For example, the overall index score 670 may range from zero to ten, with zero indicating that the physiological monitoring system 632 is performing poorly and ten indicating that the physiological monitoring system 632 is performing well, or vice-versa. In an embodiment, the processor module 581 calculates the overall index score 670 based on an individual index score generated for one or more of the indicators 652, 654, 656, 658, 660, 662, 664, and/or 668.

The processor module 581 may generate an individual index score for an indicator 652, 654, 656, 658, 660, 662, 664, or 668 based on a baseline value for the respective indicator and whether a current value for the respective indicator deviates from the baseline value. For example, a high index score may indicate that an indicator is performing well (e.g., the current value for the respective indicator is at or near the baseline value) and a low index score may indicate that an indicator is performing poorly (e.g., the current value for the respective indicator deviates from the baseline value by more than a threshold value), or vice-versa.

The overall index score 670 may be calculated based on the individual index scores of the indicators 652, 654, 656, 658, 660, 662, 664, and/or 668 and associated weights that are applied to the individual index scores. In an embodiment, the processor module 581 assigns weights to each indicator based on how much each indicator affects the overall performance of the physiological monitoring system 632. The weights may remain constant or may change over time. In one embodiment, the weights change based on a change in the current value of an indicator over a period of time. For example, a change in the value of an indicator and a change in the value of the indicator's weight may be directly or inversely proportional (e.g., if the value of an indicator increases by N %, the value of the weight may increase (or decrease) by N %). As another example, a change in the value of an indicator and a change in the value of the indicator's weight may have another type of relationship (e.g., a non-proportional relationship, a logarithmic relationship, a weight may change by a set value based on an amount of change in the value of the indicator, etc.).

As described herein with respect to FIGS. 7A-H, the indicators 652, 654, 656, 658, 660, 662, 664, and/or 668 may graphically (e.g., bar graphs, line graphs, charts, etc.) provide information about the selected physiological monitoring system 632. Additionally or in the alternative, the indicators 652, 654, 656, 658, 660, 662, 664, and/or 668 may graphically provide the individual index score for each respective indicator. In this way, by viewing the network monitoring screen 600, a user can immediately recognize which physiological monitoring systems are performing as expected, which physiological monitoring systems may face issues in the future, which physiological monitoring systems are currently facing issues, and which indicators may be responsible for any current or future issues.

Figure 7A:
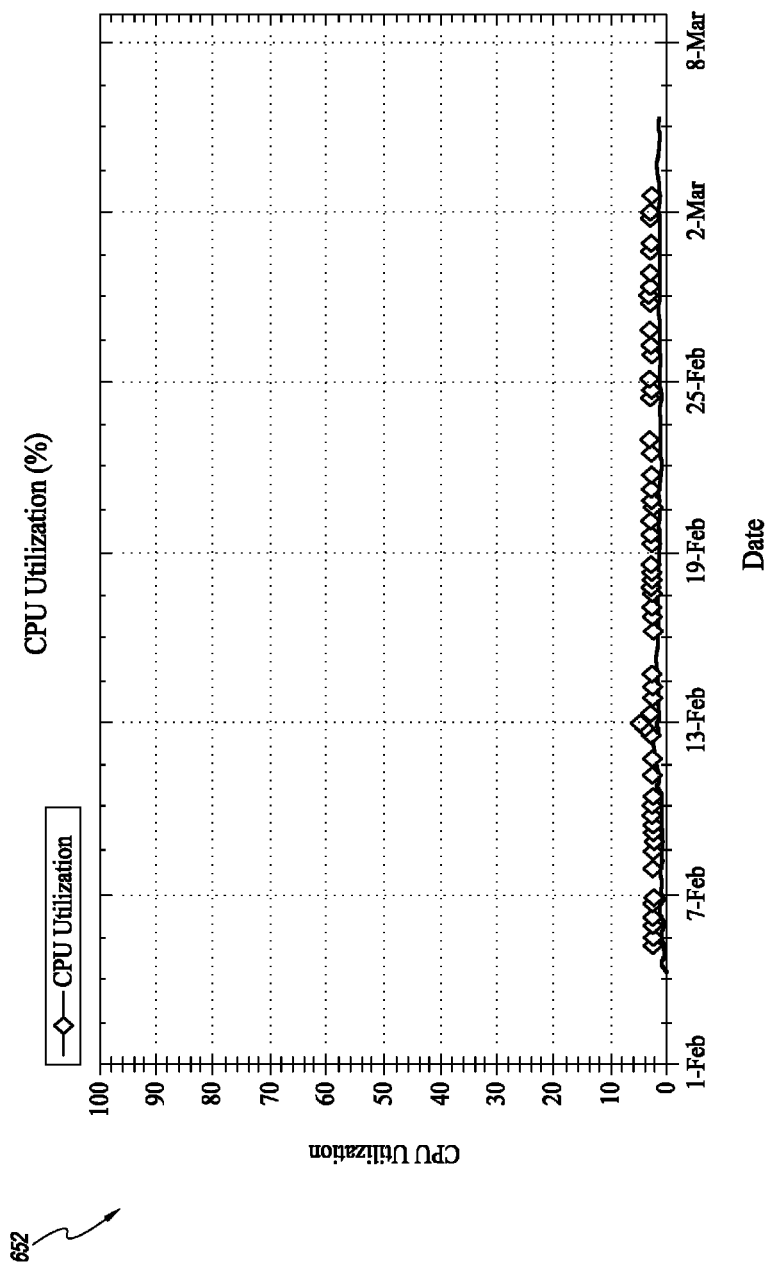
FIG. 7A is an exemplary indicator, such as one of the indicators of FIG. 6C.

FIG. 7A illustrates an example indicator, such as indicator 652 described herein with respect to FIG. 6C. Indicator 652 may graphically display the processor utilization (e.g., as a percentage) by the physiological monitoring system 632. Indicator 652 may provide such information as captured over a period of time. As illustrated in FIG. 7A, the processor utilization remains substantially constant, which may indicate that there are no current or upcoming issues.

Figure 7B:
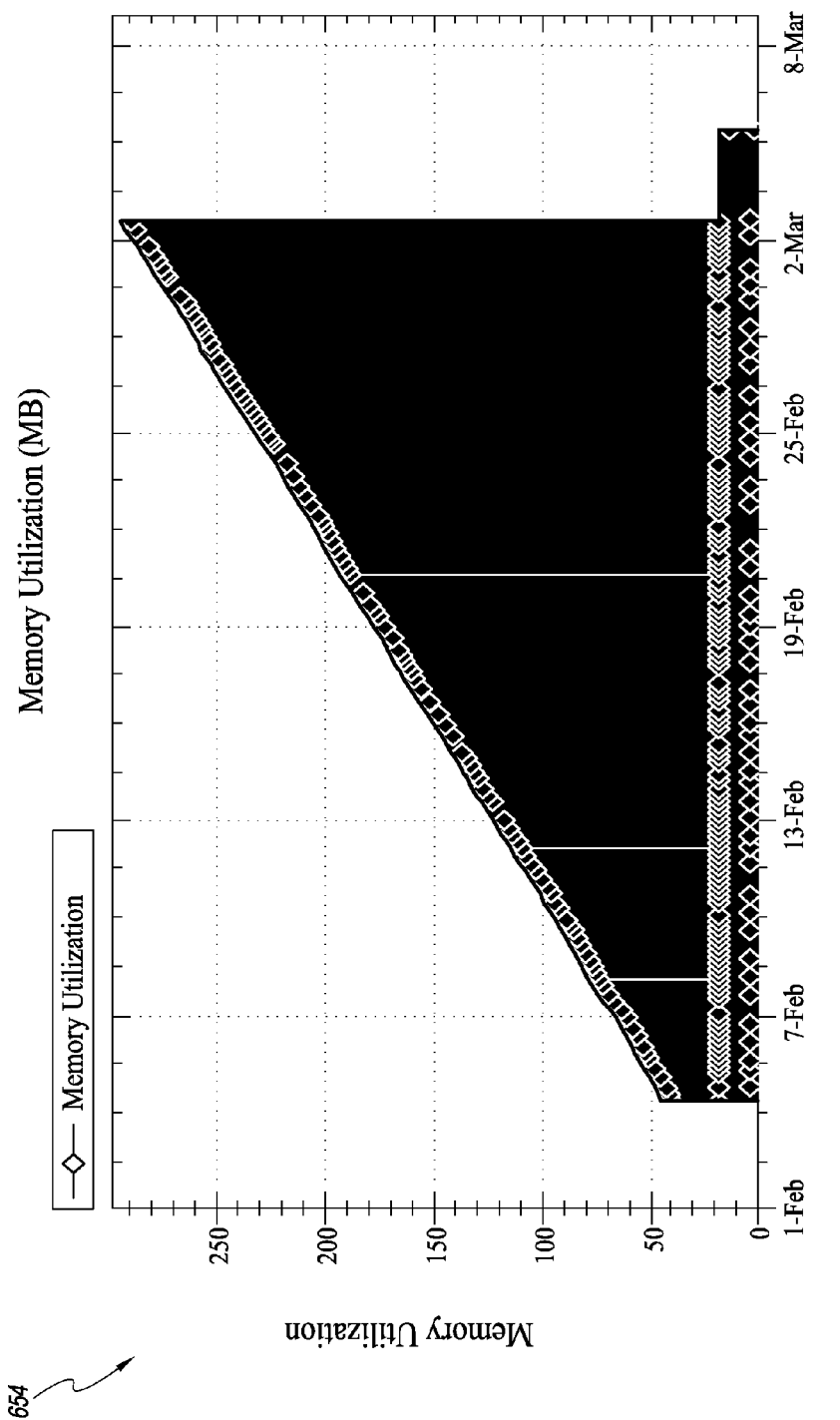
FIG. 7B is another exemplary indicator, such as one of the indicators of FIG. 6C.

FIG. 7B illustrates another example indicator, such as indicator 654 described herein with respect to FIG. 6C. Indicator 654 may graphically display the memory utilization (e.g., in megabytes) by the physiological monitoring system 632. Indicator 654 may provide such information as captured over a period of time. As illustrated in FIG. 7B, the memory utilization is steadily increasing, which may indicate that there is a current or upcoming problem with a device or other component in the physiological monitoring system 632. In such an instance, for example, the processor module 581 may generate a command to reset the physiological monitoring system 632.

Figure 7C:
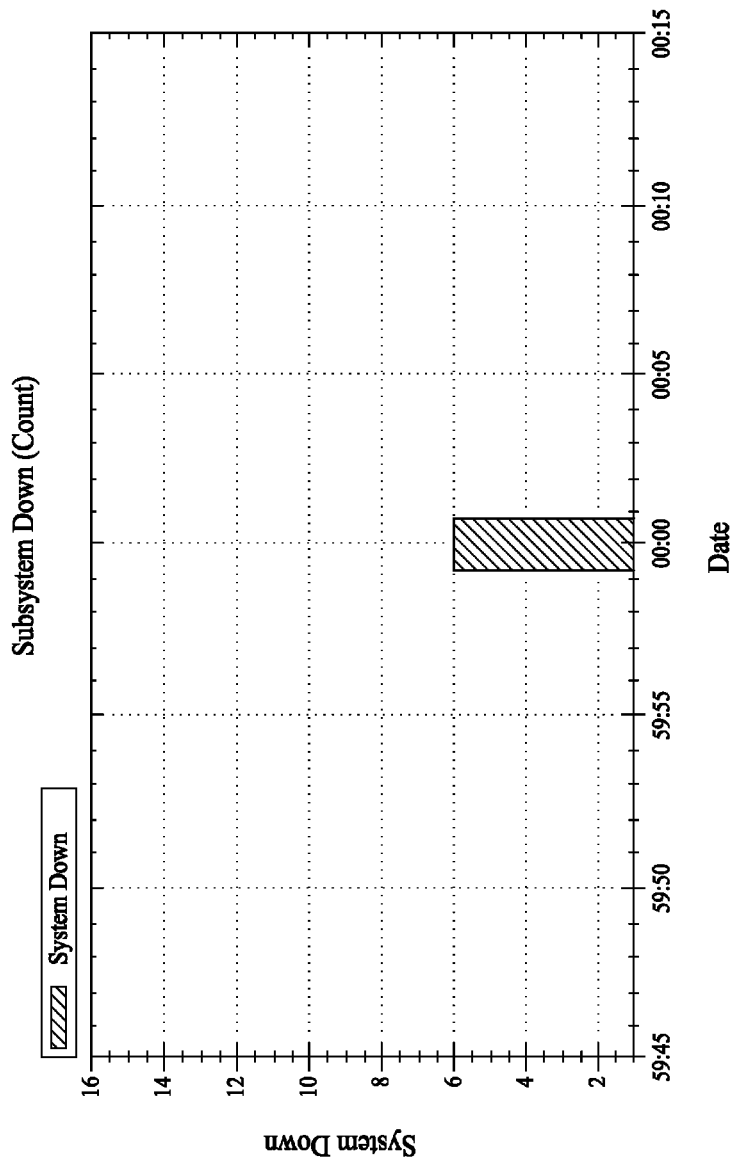
FIG. 7C is another exemplary indicator, such as one of the indicators of FIG. 6C.

FIG. 7C illustrates another example indicator, such as indicator 656 described herein with respect to FIG. 6C. Indicator 656 may graphically display the number of times a subsystem associated with the physiological monitoring system 632 failed. Indicator 656 may provide such information as captured over a period of time. As illustrated in FIG. 7C, the number of times the subsystem failed spiked at a given point in time, which may indicate that there is a current or upcoming problem and may lead to the generation of a notification.

Figure 7D:
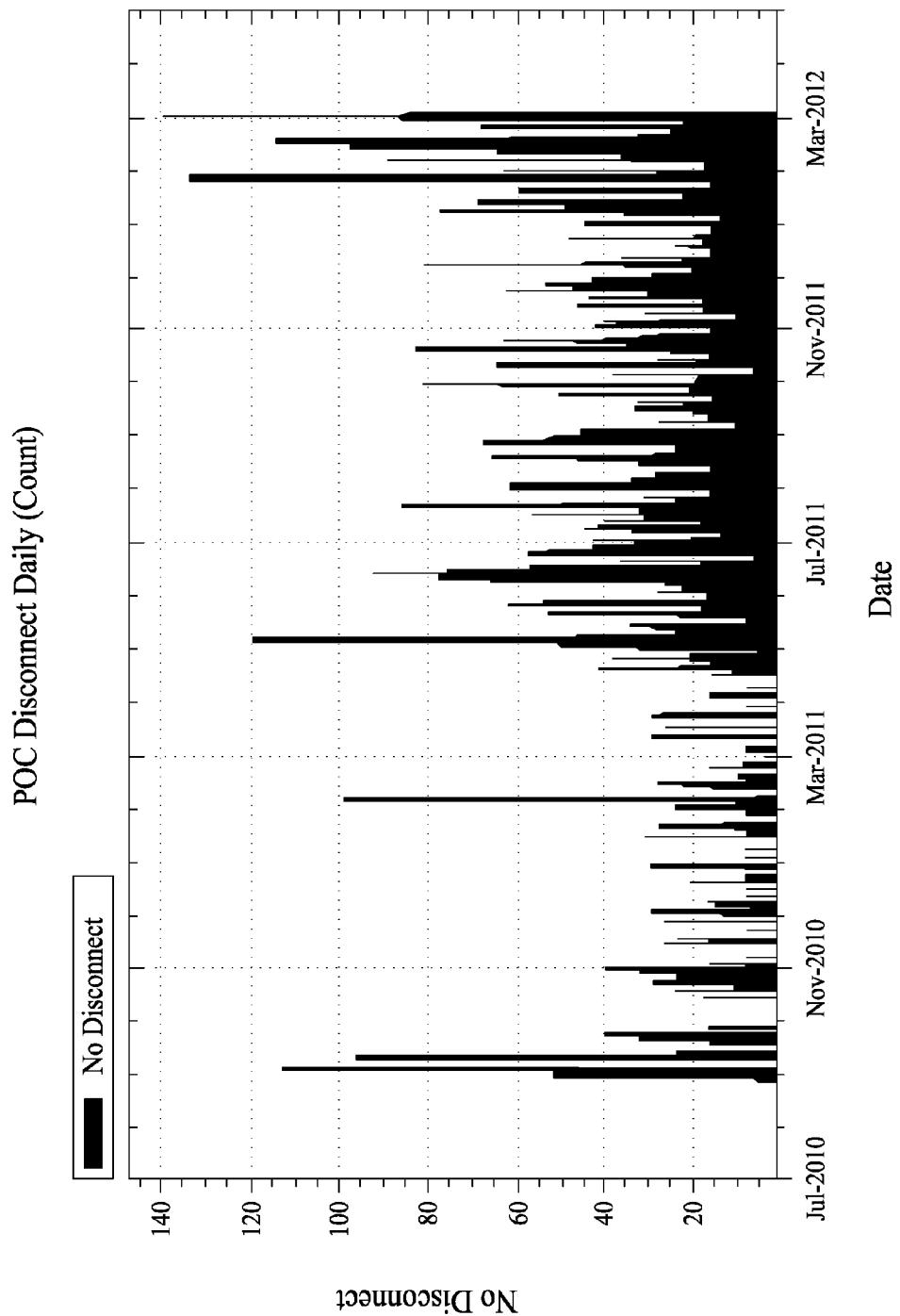
FIG. 7D is another exemplary indicator, such as one of the indicators of FIG. 6C.

FIG. 7D illustrates another example indicator, such as indicator 658 described herein with respect to FIG. 6C. Indicator 658 may graphically display the number of times a medical device disconnected from the physiological monitoring system 632. Indicator 658 may provide such information as captured over a period of time, such as a daily count. In certain embodiments, a baseline may be an average of the number of disconnects that occurred over a period of time. Deviations from the average may result in the generation of a notification.

Figure 7E:
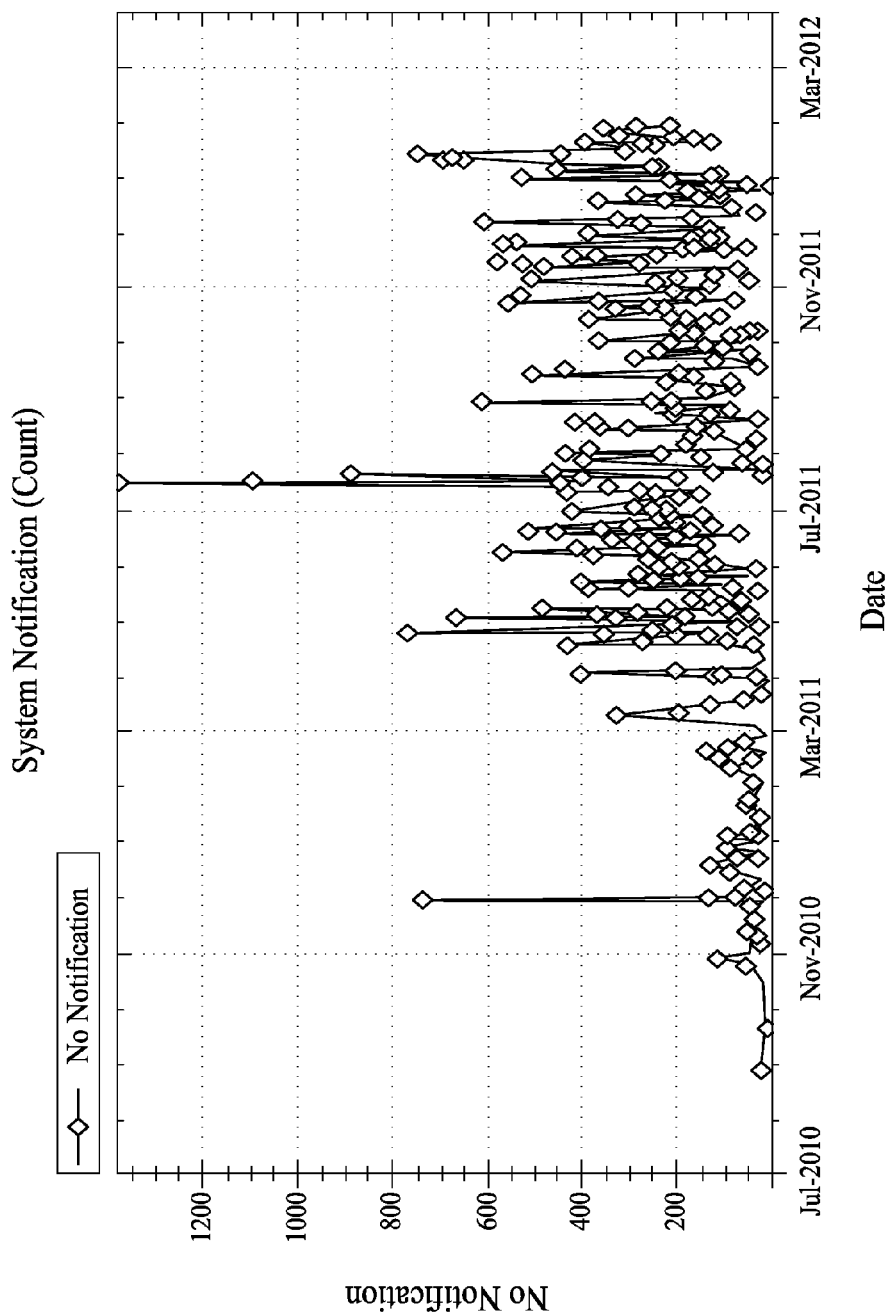
FIG. 7E is another exemplary indicator, such as one of the indicators of FIG. 6C.

FIG. 7E illustrates another example indicator, such as indicator 660 described herein with respect to FIG. 6C. Indicator 660 may graphically display the number of times a medical device generated an alarm condition in the physiological monitoring system 632. Indicator 660 may provide such information as captured over a period of time. In certain embodiments, a baseline may be an average of the number of alarm conditions that occurred over a period of time. Deviations from the average may result in the generation of a notification.

Figure 7F:
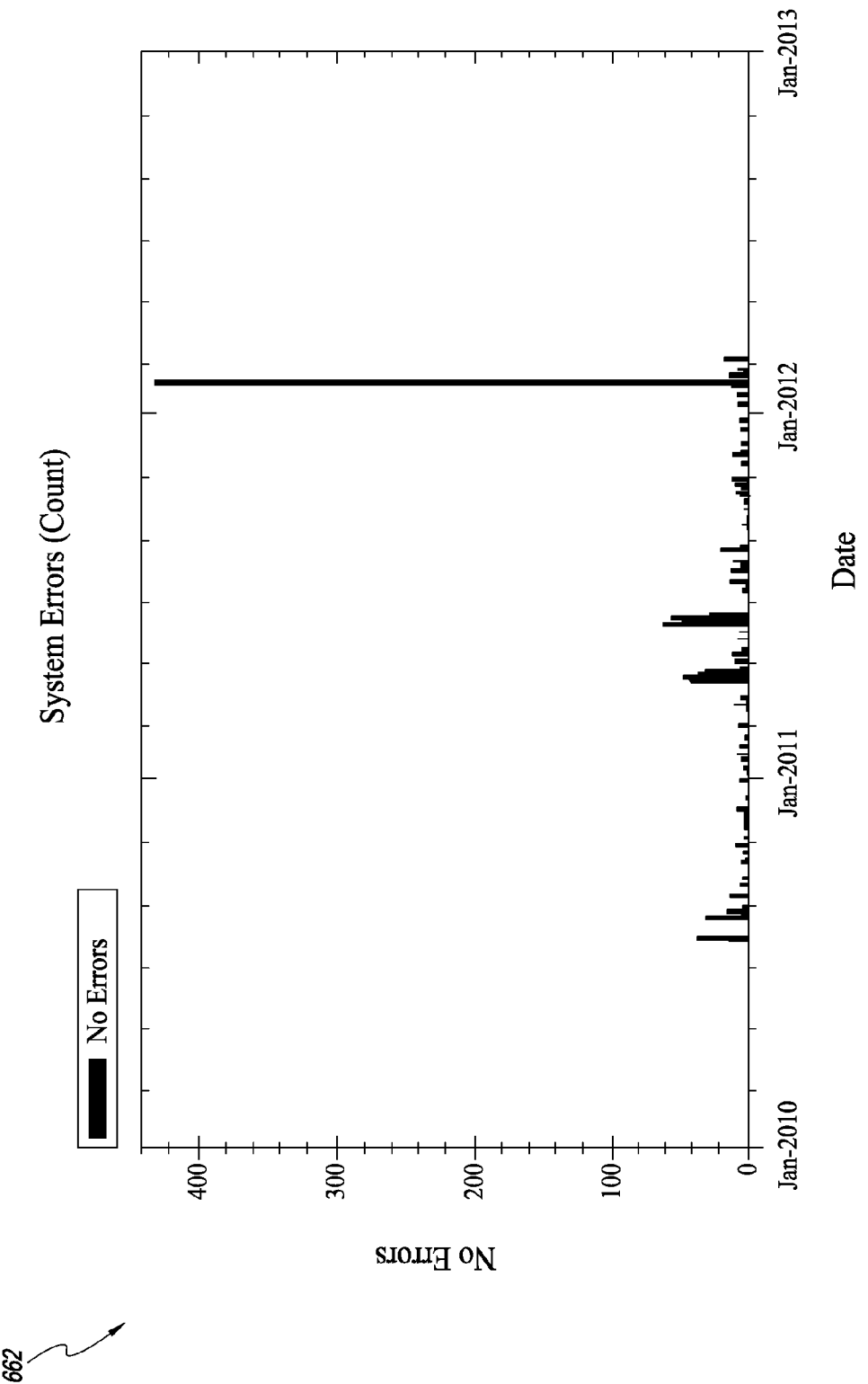
FIG. 7F is another exemplary indicator, such as one of the indicators of FIG. 6C.

FIG. 7F illustrates another example indicator, such as indicator 662 described herein with respect to FIG. 6C. Indicator 662 may graphically display the number of system errors in the physiological monitoring system 632. Indicator 662 may provide such information as captured over a period of time. In certain embodiments, a baseline may be an average of the number of system errors that occurred over a period of time. Deviations from the average may result in the generation of a notification.

Figure 7G:
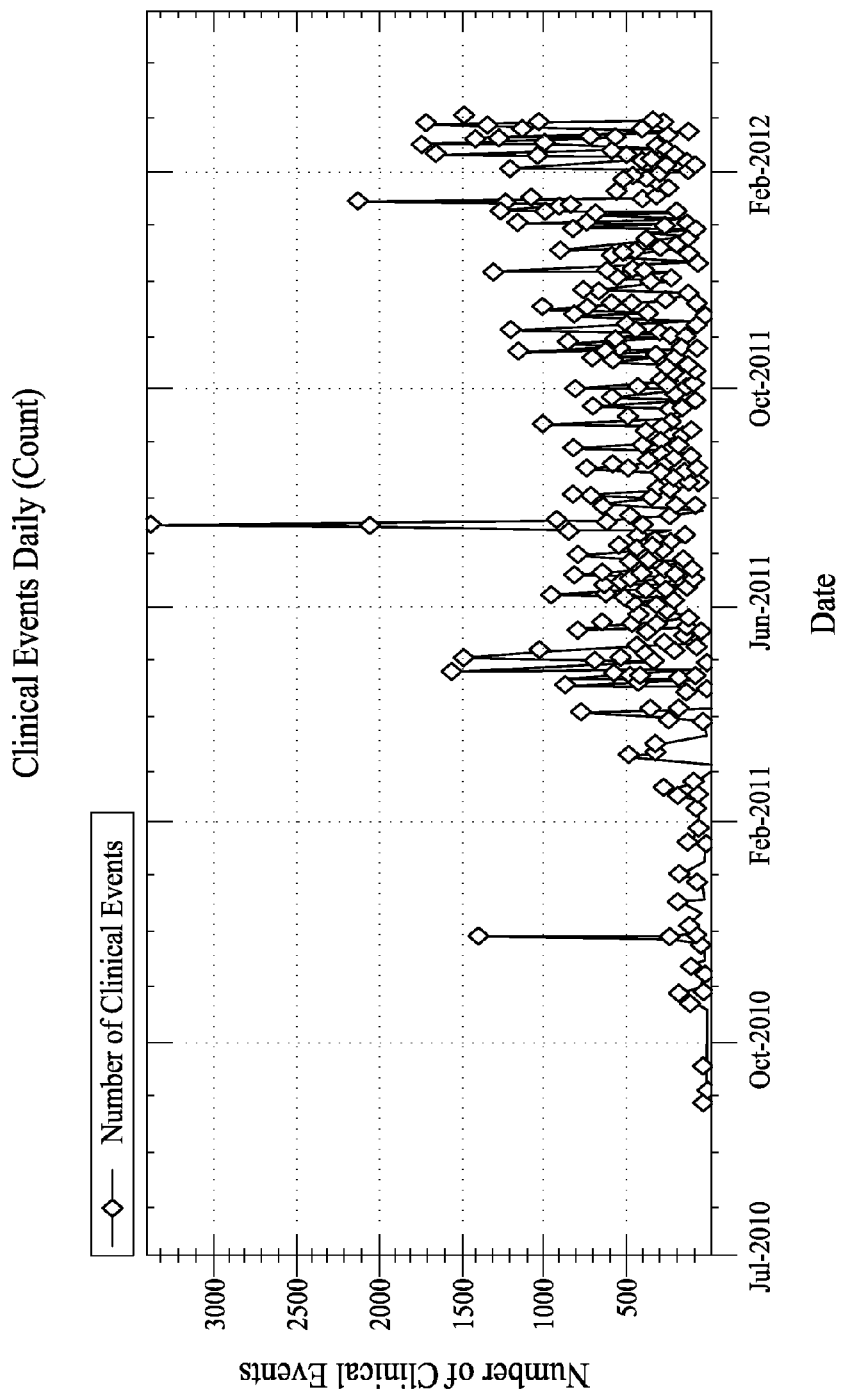
FIG. 7G is another exemplary indicator, such as one of the indicators of FIG. 6C.

FIG. 7G illustrates another example indicator, such as indicator 664 described herein with respect to FIG. 6C. Indicator 664 may graphically display the number of times a medical device within the physiological monitoring system 632 generated an alarm condition that lasted more than a predetermined amount of time. Indicator 664 may provide such information as captured over a period of time. In certain embodiments, a baseline may be an average of the number of alarm conditions that lasted more than the predetermined amount of time that occurred over a period of time. Deviations from the average may result in the generation of a notification.

Figure 7H:
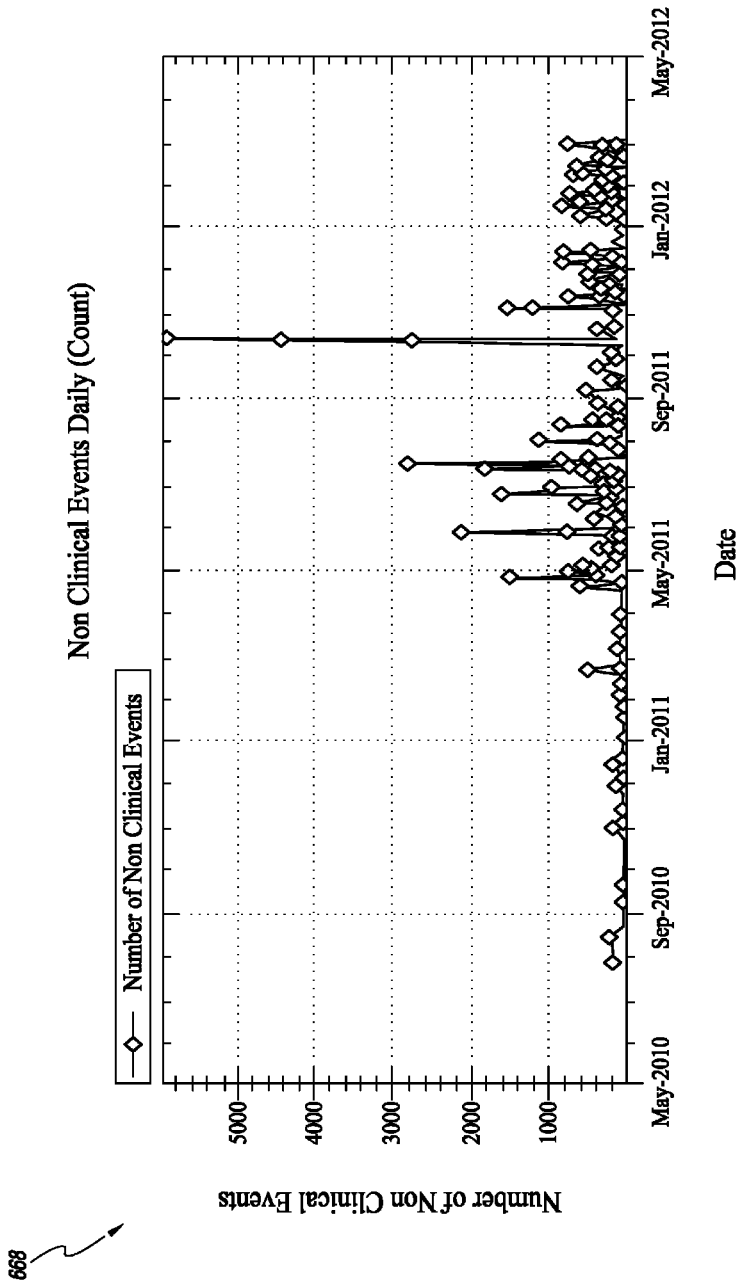
FIG. 7H is another exemplary indicator, such as one of the indicators of FIG. 6C.

FIG. 7H illustrates another example indicator, such as indicator 668 described herein with respect to FIG. 6C. Indicator 668 may graphically display the number of times a medical device within the physiological monitoring system 632 generated an alarm condition that lasted less than the predetermined amount of time. Indicator 668 may provide such information as captured over a period of time. In certain embodiments, a baseline may be an average of the number of alarm conditions that lasted less than the predetermined amount of time that occurred over a period of time. Deviations from the average may result in the generation of a notification.

Figure 8:
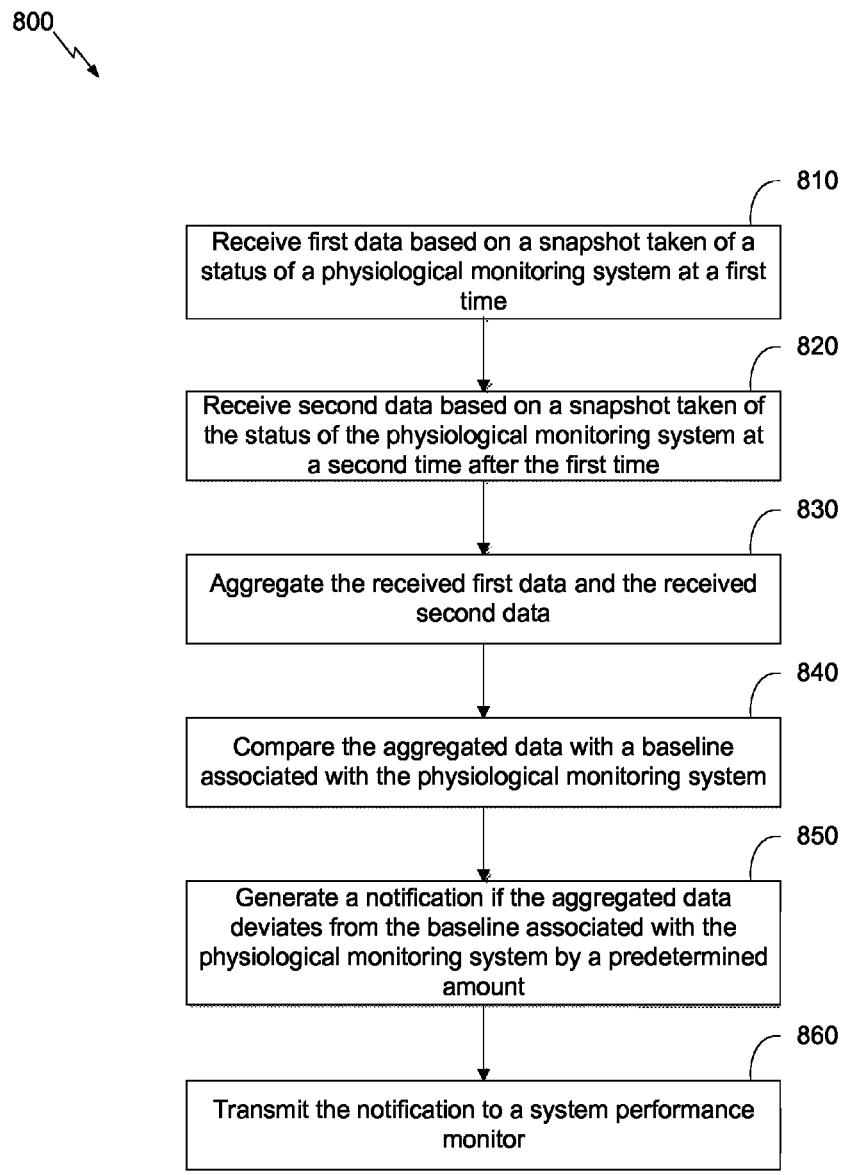
FIG. 8 is a flowchart that illustrates a process for identifying a change in system performance in a physiological monitoring system, such as the physiological monitoring system of FIG. 1.

FIG. 8 illustrates an embodiment of a process 800 for identifying a change in system performance in a physiological monitoring system. In various embodiments, additional blocks may be performed, fewer blocks than shown may be performed, and/or the blocks may be performed in an order different than that shown. The process may be performed, for example, by the network monitoring server 572 of FIG. 4.

In an embodiment, the process 800 begins at block 810. At block 810, first data based on a snapshot taken of a status of a physiological monitoring system at a first time is received. In an embodiment, the status of the physiological monitoring system comprises at least one indicator of a clinical and/or system performance of the physiological monitoring system. In some embodiments, after block 810, the process 800 proceeds to block 820. At block 820, second data based on a snapshot taken of a status of a physiological monitoring system at a second time after the first time is received. In some embodiments, after block 820, the process 800 proceeds to block 830. At block 830, the first data and the second data is aggregated. In an embodiment, like indicators of clinical and/or system performance are aggregated. In some embodiments, after block 830, the process 800 proceeds to block 840.

At block 840, the aggregated data is compared with a baseline associated with the physiological monitoring system. In an embodiment, like indicators of clinical and/or system performance are compared. In some embodiments, after block 840, the process 800 proceeds to block 850. At block 850, a notification is generated if the aggregated data deviates from the baseline by a predetermined amount. In an embodiment, the predetermined amount may be an absolute numerical value, a percentage, and/or the like. In some embodiments, after block 850, the process 800 proceeds to block 860. At block 860, the notification is transmitted to a system performance monitor. In an embodiment, the notification may include a command or instructions to perform an operation. In further embodiments, the notification identifies the medical device or other component of the physiological monitoring system that may be causing the problem. In further embodiments, the system performance monitor is one of a computing device within the physiological monitoring system or a computing device outside of the physiological monitoring system (e.g., a network monitoring server).

Information and signals described herein can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

Depending on the embodiment, certain acts, events, or functions of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, or variables.

In addition, although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

What is claimed is:

1. A method for identifying a change in system performance in one of a plurality of physiological monitoring systems, the method comprising:
   as implemented by a network monitoring system comprising computer hardware and memory, the network monitoring system in communication with the plurality of physiological monitoring systems, the network monitoring system configured with specific executable instructions,
   receiving, from a first physiological monitoring system in the plurality of physiological monitoring systems, first data based on a status of computing resources of the first physiological monitoring system at a first time, wherein each physiological monitoring system in the plurality of physiological monitoring systems comprises a plurality of patient monitoring devices, the plurality of patient monitoring devices each configured to be coupled to a different patient to measure a physiological signal of the respective patient, the plurality of patient monitoring devices configured to communicate with each other via a wireless network associated with the respective physiological monitoring system, and wherein the status of the computing resources of the first physiological monitoring system comprises at least one indicator of a system performance of the first physiological monitoring system;
   comparing the received first data with a baseline associated with the first physiological monitoring system;
   generating a notification in response to a determination that the received first data deviates from the baseline associated with the first physiological monitoring system by a predetermined amount;
   transmitting the notification to a system performance monitor; and
   displaying a location of individual physiological monitoring systems of the plurality of physiological monitoring systems, the notification, and an indication that the notification is generated for the first physiological monitoring system.

2. The method of claim 1, further comprising:
   receiving, from the first physiological monitoring system, second data based on a snapshot taken of the status of the computing resources of the first physiological monitoring system at a second time after the first time;
   aggregating the received first data and the received second data;
   comparing the aggregated data with the baseline associated with the first physiological monitoring system; and
   generating the notification if the aggregated data deviates from the baseline associated with the first physiological monitoring system by the predetermined amount.

3. The method of claim 1, further comprising:
   receiving, from the first physiological monitoring system, second data based on a snapshot taken of the status of the computing resources of the first physiological monitoring system at a second time before the first time; and
   generating the baseline associated with the first physiological monitoring system based on the received second data.

4. The method of claim 1, wherein the receiving first data comprises receiving at least one of a processor utilization by the first physiological monitoring system, a memory utilization by the first physiological monitoring system, a number of times a notification system associated with the first physiological monitoring system failed, a number of times at least one first medical device disconnected from the first physiological monitoring system, a number of times at least one second medical device generated an alarm condition, a number of errors generated by the first physiological monitoring system, a number of times the at least one second medical device generated the alarm condition that lasted more than a second predetermined amount of time, and a number of times the at least one second medical device generated the alarm condition that lasted less than the second predetermined amount of time.

5. The method of claim 1, wherein the transmitting the notification comprises transmitting a message to the system performance monitor identifying at least one component of the first physiological monitoring system that caused the generation of the notification.

6. The method of claim 1, wherein the comparing comprises comparing a selected indicator of the system performance of the first physiological monitoring system with a baseline of the selected indicator.

7. The method of claim 6, wherein the generating the notification comprises generating the notification if a value of the selected indicator deviates from the baseline of the selected indicator by the predetermined amount.

8. The method of claim 1, wherein the system performance monitor is one of a computing device within the first physiological monitoring system or a computing device outside the first physiological monitoring system.

9. The method of claim 1, further comprising displaying the received first data in response to a user selecting the first physiological monitoring system from the plurality of physiological monitoring systems.

10. A system for monitoring a first physiological monitoring system in a plurality of physiological monitoring systems, the system comprising:

a communication interface module configured to receive from the first physiological monitoring system first data based on a snapshot taken of a status of computing resources of the first physiological monitoring system at a first time, wherein the communication interface module is configured to communicate with each physiological monitoring system in the plurality of physiological monitoring systems, wherein each physiological monitoring system in the plurality of physiological monitoring systems comprises a plurality of patient monitoring devices, the plurality of patient monitoring devices each configured to be coupled to a different patient to measure a physiological signal of the respective patient, the plurality of patient monitoring devices configured to communicate with each other via a wireless network associated with the respective physiological monitoring system, and wherein the status of the computing resources of the first physiological monitoring system comprises at least one indicator of a system performance of the first physiological monitoring system;

a memory module configured to store the received first data and a baseline associated with the first physiological monitoring system;

a processor module configured to compare the received first data with the baseline associated with the first physiological monitoring system and to generate a notification in response to a determination that the received first data deviates from the baseline associated with the first physiological monitoring system by a predetermined amount; and a display module configured to display a location of individual physiological monitoring systems of the plurality of physiological monitoring systems, the notification, and an indication that the notification is generated for the first physiological monitoring system.

11. The system of claim 10, wherein the communication interface module is further configured to receive from the first physiological monitoring system second data based on a snapshot taken of the status of the computing resources of the first physiological monitoring system at a second time after the first time.

12. The system of claim 11, wherein the processor module is further configured to aggregate the received first data and the received second data, to compare the aggregated data with the baseline associated with the first physiological monitoring system, and to generate the notification if the aggregated data deviates from the baseline associated with the first physiological monitoring system by the predetermined amount.

13. The system of claim 10, wherein the communication interface module is further configured to receive from the first physiological monitoring system second data based on a snapshot taken of the status of the computing resources of the first physiological monitoring system at a second time before the first time.

14. The system of claim 13, wherein the processor module is further configured to generate the baseline associated with the first physiological monitoring system based on the received second data.

15. The system of claim 10, wherein the first data comprises at least one of a processor utilization by the first physiological monitoring system, a memory utilization by the first physiological monitoring system, a number of times a notification system associated with the first physiological monitoring system failed, a number of times at least one first medical device disconnected from the first physiological monitoring system, a number of times at least one second medical device generated an alarm condition, a number of errors generated by the first physiological monitoring system, a number of times the at least one second medical device generated the alarm condition that lasted more than a second predetermined amount of time, and a number of times the at least one second medical device generated the alarm condition that lasted less than the second predetermined amount of time.

16. The system of claim 10, wherein the communication interface module is further configured to transmit the notification to a system performance monitor identifying at least one component of the first physiological monitoring system that caused the generation of the notification.

17. The system of claim 16, wherein the system performance monitor is one of a computing device within the first physiological monitoring system or a computing device outside the first physiological monitoring system.

18. The system of claim 10, wherein the processor module is further configured to compare a selected indicator of the system performance of the first physiological monitoring system with a baseline of the selected indicator.

19. The system of claim 18, wherein the processor module is further configured to generate the notification if a value of the selected indicator deviates from the baseline of the selected indicator by the predetermined amount.

20. The system of claim 10, wherein the display module is further configured to display the received first data in response to a user selecting the first physiological monitoring system from the plurality of physiological monitoring systems.

* * * * *